(12) United States Patent
Kumagai et al.

(10) Patent No.: US 9,315,578 B2
(45) Date of Patent: Apr. 19, 2016

(54) HIGH FUNCTIONAL BISPECIFIC ANTIBODY

(75) Inventors: Izumi Kumagai, Sendai (JP); Ryutaro Asano, Sendai (JP)

(73) Assignee: TOHOKU UNIVERISTY, Sendai-Shi (JP)

( * ) Notice: Subject to any disclaimer, the term of this patent is extended or adjusted under 35 U.S.C. 154(b) by 726 days.

(21) Appl. No.: 12/225,308

(22) PCT Filed: Oct. 16, 2006

(86) PCT No.: PCT/JP2006/320571
§ 371 (c)(1),
(2), (4) Date: Jan. 13, 2009

(87) PCT Pub. No.: WO2007/108152
PCT Pub. Date: Sep. 27, 2007

(65) Prior Publication Data
US 2009/0202532 A1 Aug. 13, 2009

(30) Foreign Application Priority Data
Mar. 23, 2006 (JP) .................................. 2006-079858

(51) Int. Cl.
*A61K 39/395* (2006.01)
*C07K 16/00* (2006.01)
*C07K 16/28* (2006.01)

(52) U.S. Cl.
CPC .......... *C07K 16/2863* (2013.01); *C07K 16/2809* (2013.01); *C07K 2317/24* (2013.01); *C07K 2317/31* (2013.01); *C07K 2317/622* (2013.01); *C07K 2317/626* (2013.01)

(58) Field of Classification Search
None
See application file for complete search history.

(56) References Cited

U.S. PATENT DOCUMENTS

| 5,863,765 A | 1/1999 | Berry et al. |
| 7,960,512 B2 * | 6/2011 | Stavenhagen et al. ...... 530/387.1 |
| 2006/0210564 A1 * | 9/2006 | Kumagai et al. ............ 424/145.1 |

FOREIGN PATENT DOCUMENTS

| EP | 1454917 A2 | 9/2004 |
| JP | 2004-242638 A | 9/2004 |
| WO | WO 03/025018 A2 | 3/2003 |

OTHER PUBLICATIONS

Skolnick and Fetrow. From genes to protein structure and function: novel applications of computational approaches in the genomic era. Trends in Biotechnology, 2000. vol. 18, pp. 34-39.*
Mac Callum, Martin, and Thornton. Antibody-antigen interactions: contact analysis and binding site topography. Journal of Molecular Biology, 1996. vol. 262, pp. 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 294, pp. 151-162.*
Alt et al., "Novel tetravalent and bispecific IgG-like antibody molecules combining single chain diabodies with the immunoglobulin gamma1 Fc or CH3 region", FEBS Letters, vol. 454, 1999, pp. 90-94.
Lu et al., "A Fully Human Recombinant IgG-like Bispecific Antibody to Both the Epidermal Growth Factor Receptor and the Insulin-like Growth Factor Receptor for Enhanced Antitumor Activity", The Journal of Biological Chemistry, vol. 280, No. 20, 2005, pp. 19665-19672.
Kipriyanov et al., "Effect of Domain Order on the Activity of Bacterially Produced Bispecific Single-chain Fv Antibodies", J. Mol. Biol., vol. 330, 2003, pp. 99-111.
Kipriyanov et al., "Generation and Production of Engineered Antibodies", Molecular Biotechnology, vol. 26, 2004, pp. 39-60.
Kriangkum et al., "Bispecific and bifunctional single chain recombinant antibodies", Biomolecular Engineering, vol. 18, 2001, pp. 31-40.
Kawaguchi et al., "Construction and characterization of CHO-expressed novel recombinant bispecific antibody", The Molecular Biology Society of Japan Koen Yoshishu, vol. 28, Nov. 25, 2005, p. 769 (3P-1227 Abstract).
English Translation of International Preliminary Report on Patentability dated Jan. 12, 2008 from PCT/JP2006/320571.
EPO Supplementary European Search Report, Appl. No. EP06821877, Jun. 1, 2010, pp. 1-5.

(Continued)

*Primary Examiner* — Michael Pak
(74) *Attorney, Agent, or Firm* — Birch, Stewart, Kolasch & Birch, LLP

(57) ABSTRACT

[Problem]
The purpose of the present invention is to provide a bispecific antibody that is structurally stable, and can show alone a sufficient effect without the co-administration of activated lymphocyte (T-LAK).

[Solution]
The present invention is therefore related to a humanized highly functional bispecific antibody comprising humanized variable regions of the heavy chain (5H) and the light chain (5L) of an anti-human EGF receptor 1 antibody 528, and humanized variable regions of the heavy chain (OH) and the light chain (OL) of an anti-CD3 antibody OKT3; and having one of the following structures (i)-(vi) in Claim 1, wherein the 5H, 5L, OH and OL have an amino acid sequence represented by SEQ ID Nos 25, 26, 27 and 28, respectively.

6 Claims, 21 Drawing Sheets
(17 of 21 Drawing Sheet(s) Filed in Color)

(56) References Cited

OTHER PUBLICATIONS

Hayashi, H., et al, "A highly effective and stable bispecific diabody cancer immunotherapy: cure of xenografted tumors by bispecific diabody and T-LAK cells," Cancer Immunology and Immunotherapy, Jun. 1, 2004, vol. 53, No. 6, pp. 497-509.

Lu, D., et al, "A Fully Human Recombinant IgG-like Bispecific Antibody to Both the Epidermal Growth Factor Receptor and the Insulin-like Growth Factor Receptor for Enhances Antitumor Activity," Journal of Biological Chemistry, May 20, 2005, vol. 280, No. 20, pp. 19665-19672.

Verma, R., et al, "Antibody engineering: Comparison of bacterial, yeast, insect and mammalian expression systems," Journal of Immunological Methods, Jul. 1, 1998, vol. 216, No. 1-2, pp. 165-181.

Zuo, Z., et al, "An efficient route to the production of an IgG-like bispecific antibody," Protein Engineering, May 1, 2000, vol. 13, No. 5, pp. 361-367.

European Office Action for Appl. No. 06821877.5 dated Oct. 1, 2014.

* cited by examiner

5H (SEQ ID NO:25)

```
         10         20         30         40         50         60
CAGGTCCAACTGGTTCAGAGCGGCGCGGGCGAAGTGAAAAAGCCGGGCGCGTCGGTTAAAGTG
 Q  V  Q  L  V  Q  S  G  A  E  V  K  K  P  G  A  S  V  K  V
         70         80         90        100        110        120
AGCTGCAAAGCCTCAGGCTATACCTTTACGAGCTACTGGATGCATTGGGTTCGCCAGGCC
 S  C  K  A  S  G  Y  T  F  T  S  Y  W  M  H  W  V  R  Q  A
        130        140        150        160        170        180
CCGGGTCAGGGCCTGGAATGGATGGGTAACATTTATCCGGGCAGCGGTGGCACCAACTAT
 P  G  Q  G  L  E  W  M  G  N  I  Y  P  G  S  G  G  T  N  Y
        190        200        210        220        230        240
GCGGAAAAATTTAAGAACCGCGTGACCATGACGCGTGATACCAGCATTTCGACGGCCTAT
 A  E  K  F  K  N  R  V  T  M  T  R  D  T  S  I  S  T  A  Y
        250        260        270        280        290        300
ATGGAACTGAGCCGCCTGCGTAGCGATGACACCGCCGTGTATTACTGCGCGCGCAGTGGC
 M  E  L  S  R  L  R  S  D  D  T  A  V  Y  Y  C  A  R  S  G
        310        320        330        340        350
GGTCCGTATTTTTTCGATTACTGGGGCCAGGGCACCCTGGTTACCGTGAGCTCG
 G  P  Y  F  F  D  Y  W  G  Q  G  T  L  V  T  V  S  S
```

5L (SEQ ID No:26)

```
         10         20         30         40         50         60
GATATCGTGATGACCCAGAGCCCGCTGAGCCTGCCGGTGACCCCAGGCGAACCGGCGTCG
 D  I  V  M  T  Q  S  P  L  S  L  P  V  T  P  G  E  P  A  S
         70         80         90        100        110        120
ATTAGCTGCCGCAGCTCGCAGAACATGTGCAATAACGGCATTACCTATCTGGAATGG
 I  S  C  R  S  S  Q  N  I  V  H  N  N  G  I  T  Y  L  E  W
        130        140        150        160        170        180
TATCTGCAGAAACCGGGCAAACCCAGCTGTTAATTTATAAAGTGAGCGATCGTTT
 Y  L  Q  K  P  G  Q  S  P  Q  L  L  I  Y  K  V  S  D  R  F
        190        200        210        220        230        240
AGCGGGGTGCCGGATCGCTTTCGGCAGCGGTAGTGGCACCGATTTTACGCTGAAAATT
 S  G  V  P  D  R  F  S  G  S  G  S  G  T  D  F  T  L  K  I
        250        260        270        280        290        300
AGCCGCGTGGAAGCGGAGGATGTTGGCGTGTATTACTGCTTTCAGGGCAGCCATATCCCG
 S  R  V  E  A  E  D  V  G  V  Y  Y  C  F  Q  G  S  H  I  P
        310        320        330
CCAACTTTTGGCCAGGGCACCAAGTGAAATTAAACGC
 P  T  F  G  Q  G  T  K  V  E  I  K  R
```

OH (SEQ ID No.27)

```
         10         20         30         40         50         60
CAGGTTGAACTGGTCCAGAGCGGCGGCGTGGGCGTTGTCCAGCCGGGCCGCAGCCTGCGCCTG
 Q  V  Q  L  V  Q  S  G  G  V  V  Q  P  G  R  S  L  R  L
         70         80         90        100        110        120
TCTTGCAAAGCGAGCGGCTATACCTTTACGCGCTATACGATGCATTGGGTCCGCCAGGCG
 S  C  K  A  S  G  Y  T  F  T  R  Y  T  M  H  W  V  R  Q  A
        130        140        150        160        170        180
CCGGGCAAAGGTCTCGAATGGATTGGCTATATTAACCCGTCTCGCGGCTATACCAACTAT
 P  G  K  G  L  E  W  I  G  Y  I  N  P  S  R  G  Y  T  N  Y
        190        200        210        220        230        240
AATCAGAAAGTGAAAGATCGCTTTACCATTAGCCGCGATAACTCTAAAAACACCGCGTTT
 N  Q  K  V  K  D  R  F  T  I  S  R  D  N  S  K  N  T  A  F
        250        260        270        280        290        300
CTGCAGATGGATAGCCTGCGCCCGGAAGATACCGGCGTGTATTTTTGCGCGCGCTACTAT
 L  Q  M  D  S  L  R  P  E  D  T  G  V  Y  F  C  A  R  Y  Y
        310        320        330        340        350
GATGACCATTATAGCCTGGATTATTGGGGCCAGGGCACCCCGGTCACCGTTAGCTCG
 D  D  H  Y  Z  S  L  D  Y  W  G  Q  G  T  P  V  T  V  S  S
```

OL (SEQ ID No.28)

```
         10         20         30         40         50         60
GATATCCAGATGACCCAGAGCCCGAGCTCTCTGAGCGCGTCGGTCGGCGATCGCGTGACC
 D  I  Q  M  T  Q  S  P  S  S  L  S  A  S  V  G  D  R  V  T
         70         80         90        100        110        120
ATTACGTGCAGCGCGTCTAGCTCTGTGAGCTATATGAACTGGTACCAGCAAACCCCAGGC
 I  T  C  S  A  S  S  S  V  S  Y  M  N  W  Y  Q  Q  T  P  G
        130        140        150        160        170        180
AAAGCGAAACTGGATTTATGATACCAGCAAACTGGCGAGCGGCGTGCCGAGCCGC
 K  A  P  K  R  W  I  Y  D  T  S  K  L  A  S  G  V  P  S  R
        190        200        210        220        230        240
TTTAGCGGCTCTGGTAGCGGCACCGATTATAGTTTACCATTAGCTCTCTGCAGCCGGAA
 F  S  G  S  G  T  D  Y  T  F  T  I  S  S  L  Q  P  E
        250        260        270        280        290        300
GATATTGCGACCTATTACTGCCAGCAATGGAGCTCTAACCCGTTTACCTTTGGCCAGGGT
 D  I  A  T  Y  Y  C  Q  Q  W  S  S  N  P  F  T  F  G  Q  G
        310        320
ACCAAACTGCAGATTACCCGC
 T  K  L  Q  I  T  R
```

FIG.3-2

CH1 (SEQ ID No.29)

```
          10         20         30         40         50         60
TCGAGTGCCTCCACCAAGGGCCCATCGGTCTTCCCCCTGGCACCCTCCTCCAAGAGCACC
 S  S  A  S  T  K  G  P  S  V  F  P  L  A  P  S  S  K  S  T
          70         80         90        100        110        120
TCTGGGGGCACAGCGGCCCTGGGCTGCCTGGTCAAGGACTACTTCCCCGAACGGTCACG
 S  G  G  T  A  A  L  G  C  L  V  K  D  Y  F  P  E  P  V  T
         130        140        150        160        170        180
GTGTCGTGGAACTCAGGCGCCCTGACCAGCGGCGTGCACACCTTCCCGGCTGTCCTACAG
 V  S  W  N  S  G  A  L  T  S  G  V  H  T  F  P  A  V  L  Q
         190        200        210        220        230        240
TCCTCAGGACTCTACTCCCTCAGCAGCGTGGTGACCGTGCCCTCCAGCAGCTTGGGCACC
 S  S  G  L  Y  S  L  S  S  V  V  T  V  P  S  S  S  L  G  T
         250        260        270        280        290        300
CAGACCTACATCTGCAACGTGAATCACAAGCCCAGCAACACCAAGGTGGACAAGAAAGTT
 Q  T  Y  I  C  N  V  N  H  K  P  S  N  T  K  V  D  K  K  V
         310
GAGCCCAAATCTTGT
 E  P  K  S  C
```

PreScission Recognition Site (SEQ ID No.31)

```
          10         20
CTGGAAGTTCTGTTCCAGGGCCCC
 L  E  V  L  F  Q  G  P
```

Hinge (SEQ ID No.32)

```
          10         20         30
GACAAAACTCACACATGCCCACCGTGCCCA
 D  K  T  H  T  C  P  P  C  P
```

CH2 & CH3 (SEQ ID No.30)

```
          10         20         30         40         50         60
GCACCTGAACTCCTGGGGGGACCGTCAGTCTTCCTCTTCCCCCCAAAACCAAGGACACC
 A  P  E  L  L  G  G  P  S  V  F  L  F  P  P  K  P  K  D  T
          70         80         90        100        110        120
CTCATGATCTCCCGGACCCCTGAGGTCACATGCGTGGTGGTGGACGTGAGCCACGAAGAC
 L  M  I  S  R  T  P  E  V  T  C  V  V  V  D  V  S  H  E  D
         130        140        150        160        170        180
CCTGAGGTCAAGTTCAACTGGTACGTGGACGGCGTGGAGGTGCATAATGCCAAGACAAAG
 P  E  V  K  F  N  W  Y  V  D  G  V  E  V  H  N  A  K  T  K
         190        200        210        220        230        240
CCGCGGGAGGAGCAGTACAACAGCACGTACCGTGTGGTCAGCGTCCTCACCGTCCTGCAC
 P  R  E  E  Q  Y  N  S  T  Y  R  V  V  S  V  L  T  V  L  H
         250        260        270        280        290        300
CAGGACTGGCTGAATGGCAAGGAGTACAAGTGCAAGGTCTCCAACAAAGCCCTCCCAGCC
 Q  D  W  L  N  G  K  E  Y  K  C  K  V  S  N  K  A  L  P  A
         310        320        330        340        350        360
CCCATCGAGAAAACCATCTCCAAAGCCAAAGGGCAGCCCCGAGAACCACAGGTGTACACC
 P  I  E  K  T  I  S  K  A  K  G  Q  P  R  E  P  Q  V  Y  T
         370        380        390        400        410        420
CTGCCCCCATCCCGGGATGAGCTGACCAAGAACCAGGTCAGCCTGACCTGCCTGGTCAAA
 L  P  P  S  R  D  E  L  T  K  N  Q  V  S  L  T  C  L  V  K
         430        440        450        460        470        480
GGCTTCTATCCCAGCGACATCGCCGTGGAGTGGGAGAGCAATGGGCAGCCGGAGAACAAC
 G  F  Y  P  S  D  I  A  V  E  W  E  S  N  G  Q  P  E  N  N
         490        500        510        520        530        540
TACAAGACCACGCCTCCCGTGCTGGACTCCGACGGCTCCTTCTTCCTCTACAGCAAGCTC
 Y  K  T  T  P  P  V  L  D  S  D  G  S  F  F  L  Y  S  K  L
         550        560        570        580        590        600
ACCGTGGACAAGAGCAGGTGGCAGCAGGGGAACGTCTTCTCATGCTCCGTGATGCATGAG
 T  V  D  K  S  R  W  Q  Q  G  N  V  F  S  C  S  V  M  H  E
         610        620        630        640        650
GCTCTGCACAACCACTACACGCAGAAGAGCCTCTCCCTGTCTCCGGGTAAA
 A  L  H  N  H  Y  T  Q  K  S  L  S  P  G  K
```

FIG.3-3

CL (SEQ ID No.33)

```
        10         20         30         40         50         60
ACTGTGGCGGCCCCATCTGTCTTCATCTTCCCGCCATCTGATGAGCAGTTGAAATCTGGA
 T  V  A  A  P  S  V  F  I  F  P  P  S  D  E  Q  L  K  S  G
        70         80         90        100        110        120
ACTGCCTCTGTTGTGTGCCTGCTGAATAACTTCTATCCCAGAGAGGCCAAAGTACAGTGG
 T  A  S  V  V  C  L  L  N  N  F  Y  P  R  E  A  K  V  Q  W
       130        140        150        160        170        180
AAGGTGGATAACGCCCTCCAATCGGGTAACTCCCAGGAGAGTGTCACAGACCAGGACAGC
 K  V  D  N  A  L  Q  S  G  N  S  Q  E  S  V  T  E  Q  D  S
       190        200        210        220        230        240
AAGGACAGCACCTACAGCCTCAGCAGCACCCTGACGCTGAGCAAAGCAGACTACGAGAAA
 K  D  S  T  Y  S  L  S  S  T  L  T  L  S  K  A  D  Y  E  K
       250        260        270        280        290        300
CACAAAGTCTACGCCTGCGAAGTCACCCATCAGGGCCTGAGCTCGCCCGTCACAAAGAGC
 H  K  V  Y  A  C  E  V  T  H  Q  G  L  S  S  P  V  T  K  S
       310
TTCAACAGGGGAGAGTGT
 F  N  R  G  E  C
```

G1 linker (SEQ ID No.34)

```
        10
GCCGGCGGGGGCGGTTCG
 A  G  G  G  G  S
```

G3 linker (SEQ ID No.35)

```
        10         20         30         40
GCCGGCGGGGGCGGTAGCGGCGGCGGGGGCGGTCGCGGCGGTCGGCGGGGGGTCGCCGGATCG
 A  G  G  G  G  S  G  G  G  G  S  G  G  G  G  S
```

G4 linker (SEQ ID No.36)

```
        10         20         30         40         50         60
GCCGGGCTGCAGGTGTGGTGGTTCTGGTGGTGGTTCTGGCGGCGGGGGCGGCTCCGGT
 A  A  A  A  G  G  G  G  S  G  G  G  G  S  G  G  G  G  S  G
        70
GGTGGTGGATCC
 G  G  G  S
``` c-myc & His tag (SEQ ID No.38)

```
        10         20         30         40         50         60
GCCGCGGCTGCAGAACAAAACTCATCTCAGAAGAGGATCTGAATCTAGGGGGGTGGCATG
 A  A  A  A  E  Q  K  L  I  S  E  E  D  L  N  L  G  G  G  M
        70         80
CGCGGGCTCGCACCATCATCATCACCACCAT
 R  G  S  H  H  H  H  H  H
``` signal peptide (SEQ ID No.37)

```
        10         20         30         40         50
ATGGATTGGGTGTGGACCTTGCTATTCCTGTTGTCAGTAACTGCAGGTGTCCACTCC
 M  D  W  V  W  T  L  L  F  L  L  S  V  T  A  G  V  H  S
```

FIG.3-4

HIGH FUNCTIONAL BISPECIFIC ANTIBODY

FIELD OF THE INVENTION

The present invention is related to a humanized highly functional bispecific antibody, which may be used in a cancer-specific immunotherapy, a single-chain polypeptide constituting the antibody, a nucleic acid encoding the polypeptide, a method for the production of the antibody, use of them as a pharmaceutical preparation, etc.

BACKGROUND OF THE INVENTION

Surgical resection, chemotherapy, radiotherapy and immunotherapy have been mainly used alone or together as a method for treating cancer (malignant tumor). Among them, the immunotherapy has a lot of potentialities and is therefore expected to make further progress in the near future although it is still in a developmental stage now.

The cancer-specific immunotherapy the means a treating method in which a cytotoxic activity is affected only upon cancer cells. As a drug showing the cytotoxic activity is combined with an antibody so as to have directivity in this therapy, it is now called a "missile therapy." Studies have now been carried out by targeting a substance that is abnormally expressed in the cancer cells or that will change according to malignant alternation or canceration of cells and using said substance as an antigen that will be effectively used for the preparation of the antibody with a minimum of side effects. Such antigen is called a cancer-associated antigen.

Among antibodies with multiple specificities, an antibody with bispecificity (Bispecific Antibody: BsAb) has been studied intensively. The bispecific antibody can bind specifically to two different kinds of antigens so that it will be utilized as a therapeutic agent having a specific anti-cancer effect. A diabody (Db) is a minimum unit of the above bispecific antibody. It was developed by utilizing the property that the variable region in a heavy chain (VH) and the variable region in a light chain (VL) derived from the same parent antibody will form a hetero-dimer through non-covalent bond (Hollinger, et al., Proc. Natl. Acad. Sci. USA 90, 6444-6448, 1993).

The diabody-type bispecific antibody is characterized by having low immunogenicity and high infiltrating activity into tumor tissues due to its low molecular weight (ca. 60,000), and by being able to be easily mass-produced at a low cost with use of microorganisms such as *E. coli*, and to be easily altered in function by means of genetic engineering.

The present inventors already found that the diabody-type bispecific antibody (Ex3), which was produced by utilizing an anti-human EGF receptor 1 (Her 1) antibody 528 and an anti-CD3 antibody OKT3, and its humanized diabody-type bispecific antibody (referred to as "hEx3" in Patent Document 1) showed an extremely strong anti-tumor effects. It was further speculated that the structural stability of the variable regions of the above antibodies 528 and OKT3 themselves and their combination are very important for showing such advantageous effects by comparison with an diabody-type bispecific antibody prepared using other antibodies.

Methods for the production of bispecific antibodies other than the diabody-type bispecific antibody are described in Non-Patent Documents 1 and 2.
Patent Document 1: Japanese Patent Publication No. 2004-242638
Non-Patent Document 1: Alt M, et. al. Novel tetravalent and bispecific IgG-like antibody molecules combining single-chain diabodies with the immunoglobulin gamma1 Fc or CH3 region. *FEBS Lett.*, 454, 90-4. (1999)
Non-Patent Document 2: Lu D, et. al. A fully human recombinant IgG-like bispecific antibody to both the epidermal growth factor receptor and the insulin-like growth factor receptor for enhanced antitumor activity. J Biol. Chem., 280, 19665-72. (2005)

DISCLOSURE OF THE INVENTION

Problem to be Solved by the Invention

However, it is still desired to further alter or improve the humanized diabody-type bispecific antibody (hEx3) in order to increase the structural stability and to show sufficient effects even with a single administration without resorting to co-administration with an activated lymphocyte (T-LAK), so that it may be further developed as a treating agent. The main purpose of the present invention is therefore to provide a bispecific antibody having such advantageous functions.

Means for Solving the Problems

The present inventors have studied to resolve the above problems and provide a highly functional hEx3, and finally succeeded in preparing six kinds of humanized bispecific antibodies (BsAb) and completed the present invention. The humanized diabody-type bispecific antibody will be referred to also just as "Ex3" below in the present specification.

The present invention is therefore related to the following aspects:
[1] A humanized highly functional bispecific antibody comprising humanized variable regions of the heavy chain (5H) and the light chain (5L) of an anti-human EGF receptor 1 antibody 528, and humanized variable regions of the heavy chain (OH) and the light chain (OL) of an anti-CD3 antibody OKT3; and having one of the following structures:
(i) (OH5L)-(a peptide linker)-(5HOL);
(ii) an antibody wherein a humanized diabody-type bispecific antibody consisting of two kinds of the single-chain polypeptides of (OH5L) and (5HOL) is bonded to two Fc regions of a human antibody via each hinge region through either of the two single-chain polypeptides;
(iii) an antibody wherein any one of the single-chain polypeptides of (OH5L)-(a peptide linker)-(5HOL), (OH5H)-(a peptide linker)-(5LOL), or (5L5H)-(a peptide linker)-(OHOL) is bonded to two Fc regions of a human antibody via each hinge region;
(iv) an antibody wherein each VH and VL of a human antibody are replaced by a single-chain Fv (5HL) comprising humanized variable regions of the heavy chain (5H) and the light chain (5L) of an anti-human EGF receptor 1 antibody 528, and a single-chain Fv (OHL) comprising humanized variable regions of the heavy chain (OH) and the light chain (OL) of an anti-CD3 antibody OKT3, respectively, or vice versa;
(v) (OH5H)-(a peptide linker)-(5LOL); or
(vi) (5L5H)-(a peptide linker)-(OHOL),
wherein the 5H, 5L, OH and OL have an amino acid sequence represented by SEQ ID Nos 25, 26, 27 and 28, respectively; or an amino acid sequence in which one or a few amino acids are substituted, deleted, inserted or added in said amino acid sequences and having substantially the same antigen-binding property as that of said variable region.
[2] The humanized highly functional bispecific antibody of the aspect [1] having the structure (ii), wherein the humanized diabody-type bispecific antibody is bonded to the hinge regions via a protease cleavage site.

[3] The humanized highly functional bispecific antibody of the aspect [1] having the structure (iii), wherein the single-chain polypeptide is bonded to the hinge regions via a protease cleavage site.

[4] A polypeptide constituting the humanized highly functional bispecific antibody of the aspect [1] having the structure (ii), which consists of the polypeptide (OH5L) or (5HOL) that is bonded to the Fc region of the human antibody via its hinge region.

[5] A polypeptide constituting the humanized highly functional bispecific antibody of the aspect [1] having the structure (iii).

[6] An either polypeptide of the two kinds of polypeptides constituting the humanized highly functional bispecific antibody of the aspect [1] having the structure (iv).

[7] A nucleic acid molecule encoding the humanized highly functional bispecific antibody of the aspect [1] having the structure (i), or the single-chain polypeptide of any one of the aspects [4], [5] and [6].

[8] A replicable cloning vector or an expression vector containing the nucleic acid molecule of the aspect [7].

[9] The vector of the aspect [8], which is a plasmid vector.

[10] A host cell transformed with the vector of the aspect [9] or [10]

[11] The hose cell of the aspect [10], which is a mammalian cell.

[12] A method for the production of the humanized highly functional bispecific antibody of the aspect [1] having the structure (i), comprising culturing the host cell according to the aspect [11] to express the nucleic acid in it, collecting and purifying the single-chain polypeptide according to the aspect [4], [5] or [6].

[13] A method for the production of the humanized highly functional bispecific antibody of the aspect [1] having the structure (ii) or (iv), comprising assembling the two kinds of the single-chain polypeptides produced by the method of the aspect [12] to form said antibody.

[14] A method for the production of the humanized diabody-type bispecific antibody consisting of two kinds of the single-chain polypeptides of (OH5L) and (5HOL) or the humanized highly functional bispecific antibody of the aspect [1] having the structure (i), comprising digesting the humanized highly functional bispecific antibody of the aspect [2] or [3] with a protease to cleave it between the Fc region and the hinge region.

[15] A pharmaceutical composition comprising the humanized highly functional bispecific antibody of any one of the aspects [1]-[3] as an active ingredient.

[16] The pharmaceutical preparation of the aspect [1,5] for use in eliminating, hurting, damaging and/or reducing tumor cells.

Advantages of the Invention

The humanized highly functional bispecific antibody according to the present invention is prepared by highly functionalizing Ex3. Thus, the present humanized highly functional bispecific antibody has a significantly increased cytotoxicity and an increased stability when compared with Ex3, and is further provided with an inducing property of an antibody-dependent cellular cytotoxicity (ADCC) and a cell-dependent cytokine (CDC). It has a divalent binding activity with an antigen. A bispecific antibody with a minimized additional sequence such as Tag may be easily prepared by digestion with a protease, and easily purified with Protein A.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3-1 shows examples of the amino acid sequences of the variable regions 5H and 5L, which are a domain constituting the humanized highly functional bispecific antibody.

FIG. 3-2 shows examples of the amino acid sequences of the variable regions OH and OL, which are a domain constituting the humanized highly functional bispecific antibody.

FIG. 3-3 shows examples of the amino acid sequences of the CH1, CH2 & CH3, PreSission-recognition sequence, and Hinge sequence, which are a domain constituting the humanized highly functional bispecific antibody.

FIG. 3-4 shows examples of the amino acid sequences of the CL, various linkers, the signal peptide, and c-myc & His tag, which are a domain constituting the humanized highly functional bispecific antibody.

FIG. 4-1 are photos of SDS-PAGE and Western blotting showing the results of purification of the humanized highly functional bispecific antibody.

FIG. 4-2 are photos of SDS-PAGE and Western blotting showing the results of purification of the humanized highly functional bispecific antibody.

BEST MODE FOR CARRYING OUT THE INVENTION

Figure 1:
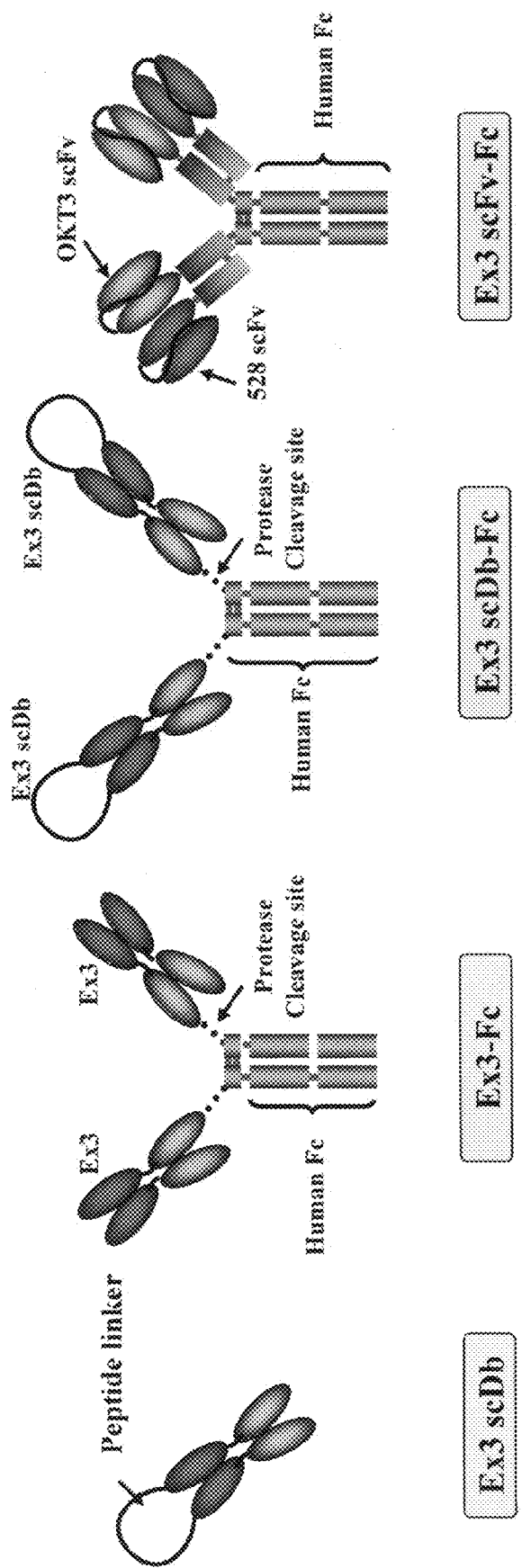
FIG. 1 shows the structure and main features of the humanized highly functional bispecific antibody according to the present invention.

The humanized highly functional bispecific antibody according to the present invention (referred to hereinafter also as "the present BsAb") comprises the humanized variable regions of the heavy chain (5H) and the light chain (5L) of an anti-human EGF receptor 1 antibody 528, and the humanized variable regions of the heavy chain (OH) and the light chain (OL) of OKT3, an antibody against a surface antigen (CD3) expressed by a cytotoxic T cell. The structures and main features are shown in FIG. 1.

The first type of the present BsAb (i) (Ex3 scDb) has a structure represented by (OH5L)-(a peptide linker)-(5HOL). Thus, the two kinds of the polypeptide chains constituting Ex3, OH5L and 5HOL, are further linked together by the peptide linker to form a single polypeptide chain as a whole. As a result, the structure of this BsAb molecule has been more stabilized than Ex3. Furthermore, said BsAb may be produced by a single kind of an expression vector, so that more homogeneous BsAb molecule may be prepared than Ex3. The term "scDb" means a single-chain diabody-type bispecific antibody.

Any linker known in the art or one modified therefrom may be optionally selected and used as the peptide linker in the present invention without any limitation in its length as long as it can assemble OH and OL, or 5H and 5L together to form an antigen-binding site that can specifically react with the respective antigen. The peptide linker may have about 1-20 amino acids, preferably about 1-15 amino acids, more preferably about 2-10 amino acids.

The above peptide linker may be inserted between 5H and 5L, or between OH and OL. And either VL or VH in each unit of Ex3 may be positioned at its N-end. Thus, the first type of the present BsAb comprises each variable region in the order of (1)N-end:OH-5L-(the peptide linker)-5H-OL:C-end; (2) N-end:5H-OL-(the peptide linker)-OH-5L:C-end; (3) N-end: 5L-OH-(the peptide linker)-OL-5H:C-end, or (4) N-end:OL-5H-(the peptide linker)-5L-OH:C-end.

The second type of the present BsAb (ii) (Ex3-Fc) has the structure wherein the humanized diabody-type bispecific antibody (Ex3) consisting of the two kinds of the single-chain polypeptides of (OH5L) and (5HOL) is bonded to the two Fc regions of the human antibody via each hinge region through either of the two single-chain polypeptides. Thus, this BsAb is composed of one of the two kinds of the single-chain polypeptide constituting Ex3, which is bonded to the Fc region of the human antibody via each hinge region (for example, (5HOL)-(hinge region)-Fc region), and the other polypeptide (for example, OH5L). The above antibody may be produced by expressing the two kinds of the single-chain polypeptides and assembling them. The term "Fc region" means two domains (CH2 and CH3) located at C-end of the heavy chain constituting a constant region (C region).

Either 5HOL or OH5L may be bonded to the Fc region of the human antibody via the hinge region. And, either the heavy or light chain variable region in each single polypeptide chain may be bonded with the hinge region.

The third type of the present BsAb (iii) (Ex3 scDb-Fc) has the structure wherein the single-chain polypeptide of the first type of the present BsAb (i) (Ex3 scDb), the fifth type of the present BsAb (v) or the sixth type of the present BsAb (vi) is bonded to the two Fc regions of the human antibody via each hinge region instead of Ex3 in the second type of the present BsAb (ii). (OH5L)-(the peptide linker)-(5HOL), (OH5H)-(the peptide linker)-(5LOL), or (5L5H)-(the peptide linker)-(OHOL) may be bonded with the hinge region through any one of the two kinds of the heavy or light chain variable regions in the above single polypeptide chains.

As the number of the domains constituting the second and third type of the present BsAb is the same as that of an immunoglobulin molecule, it is considered that these BsAb have a space structure similar to that of the immunoglobulin molecule. Furthermore, by inserting a protease cleavage site between the hinge region and Ex3 or Ex3 scDb in the second or third type of the present BsAb, Ex3 or Ex3 scDb can be easily produced by digesting these BsAb with the protease followed by the purification steps mentioned below. The Ex3 or Ex3 scDb thus produced by the protease digestion will show stronger cytotoxicity than those produced by the conventional methods.

The fourth type of the present BsAb (iv) (Ex3 scFv-Fc) has the structure wherein the VH and VL of the human antibody are replaced by the single-chain Fv (scFv) (5HL) comprising the humanized variable regions of the heavy chain (5H) and the light chain (5L) of the anti-human EGF receptor 1 antibody 528, and the single-chain Fv (OHL) comprising the humanized variable regions of the heavy chain (OH) and the light chain (OL) of an anti-CD3 antibody OKT3, respectively, or vice versa. Thus, this BsAb is an IgG-type immunoglobulin composed of two polypeptides, i.e., a polypeptide wherein one of the scFv of OHL and 5HL is bonded to the N-end of CH1 domain constituting the constant region of the heavy chain, and a polypeptide wherein the other scFv is bonded to the N-end of CL domain constituting the constant region of the light chain. And, either the heavy or light chain variable region in each scFv may be bonded with the hinge region. The above antibody may be produced by expressing the two kinds of the single-chain polypeptides and assembling them.

As any one of the present BsAb of the types (ii), (iii) and (iv) comprises the human Fc region, it may be easily purified with Protein A. They will further induce an antibody-dependent cellular cytotoxicity (ADCC) and cell-dependent cytokine (CDC). They also show an advantage that they can bind divalently to each antigen, which is not found with Ex3.

The fifth type of the present BsAb (v) has the structure of (OH5H)-(the peptide linker)-(5LOL). Thus, a polypeptide chain consisting of two kinds of the heavy chain, and a polypeptide chain consisting of two kinds of the light chain are combined together via the peptide linker to form a single polypeptide chain as a whole.

Any linker known in the art or one modified therefrom may be optionally selected and used as the peptide linker in the present invention without any limitation in its length as long as it can assemble OH and OL, or 5H and 5L together to form an antigen-binding site that can specifically react with the respective antigen. The peptide linker may have about 1-20 amino acids, preferably about 1-15 amino acids, more preferably about 2-10 amino acids.

The above peptide linker may be inserted between 5H and 5L, or between OH and OL. And any domain in each single-chain polypeptide may be positioned at its N-end. Thus, the fifth type of the present BsAb comprises each variable region in the order of: (1)N-end:OH-5H-(the peptide linker)-5L-OL: C-end; (2) N-end:5L-OL-(the peptide linker)-OH-5H:C-end;

(3) N-end:5H—OH-(the peptide linker)-OL-5L:C-end, or (4) N-end:OL-5L-(the peptide linker)-5H—OH:C-end.

The sixth type of the present BsAb (vi) (Ex3 tandem scFv) has the structure of (5L5H)-(the peptide linker)-(OLOH). Thus, the single-chain Fv (528 scFv) (5HL) comprising the humanized variable regions of the heavy chain (5H) and the light chain (5L) of the anti-human EGF receptor 1 antibody 528, and the single-chain Fv (OKT3 scFv) (OHL) comprising the humanized variable regions of the heavy chain (OH) and the light chain (OL) of the anti-CD3 antibody OKT3 are linked tandem together via the peptide linker to form a single polypeptide chain as a whole. The peptide linker used in this type is the same as that used in the fifth type of the present BsAb. Either 528 scFv or OKT3 scFv may be positioned at the N-end of the single-chain polypeptide. Furthermore, either heavy chain or light chain may be positioned at the N-end of each scFv. Considering the order of the two kinds of heavy chains and light chains, the sixth type of the present BsAb includes eight kinds of single-chain polypeptides in total.

At least one of the two polypeptides in Ex3 constituting the present BsAb may comprise a linker that links the variable region of the heavy chain (VH) and the variable region of the light chain (VL) with each other. The term "linker" as used herein refers to an oligopeptide or polypeptide that combines VH and VL together to give a single-chain polypeptide. The linker is preferably a peptide linker. Any linker known in the art or one modified therefrom may be optionally selected and used in the present invention as long as it can operably combine the two polypeptides together to give the single-chain polypeptide. The peptide linker according to the present invention may have about 1-50 amino acids, preferably about 2-30 amino acids, more preferably about 2-20 amino acids. The term "operably combine" as used herein refers to an appropriate folding of the polypeptide to give a fused protein having such a three-dimensional structure as to mimic the function of the original protein (the function derived from the original polypeptide or protein) such as all or part of its biological activity.

The length of the linker is selected so as to give a desired activity to the single-chain polypeptide or fused protein while depending on their properties. The linker, however, should be long enough to fold the resulting single-chain polypeptide so as to give the desired biological activities. The length of the linker may be experimentally determined by testing a series of single-chain polypeptides prepared by using linkers with different lengths. The documents listed above with respect to the diabody and techniques for its production may be referred to for the linker as well.

The VH region and VL region may be arbitrarily allocated in the single-chain polypeptide, including VL(N-end)-Linker-VH(C-end) construct and VH (N-end)-Linker-VL (C-end) construct.

The amino acid sequences represented by SEQ ID Nos 25, 26, 27 and 28 (FIG. 3-2) are representative examples of the four humanized variable regions constituting the present BsAb, i.e., 5H, 5L, OH and OL, respectively.

There is no limitation on the constant region or Fc region comprised in the present BsAb as long as it is derived from the human antibody. For example, CL may be derived from κ or λ chain. Fc region or the heavy chain constant region is usually derived from γ chain of IgG. The amino acid sequences represented by SEQ ID Nos 29, 30 and 33 (FIG. 3-3, 3-4) are representative examples of CH1, CH2 & CH3, and CL, respectively.

Figures 1, 4:
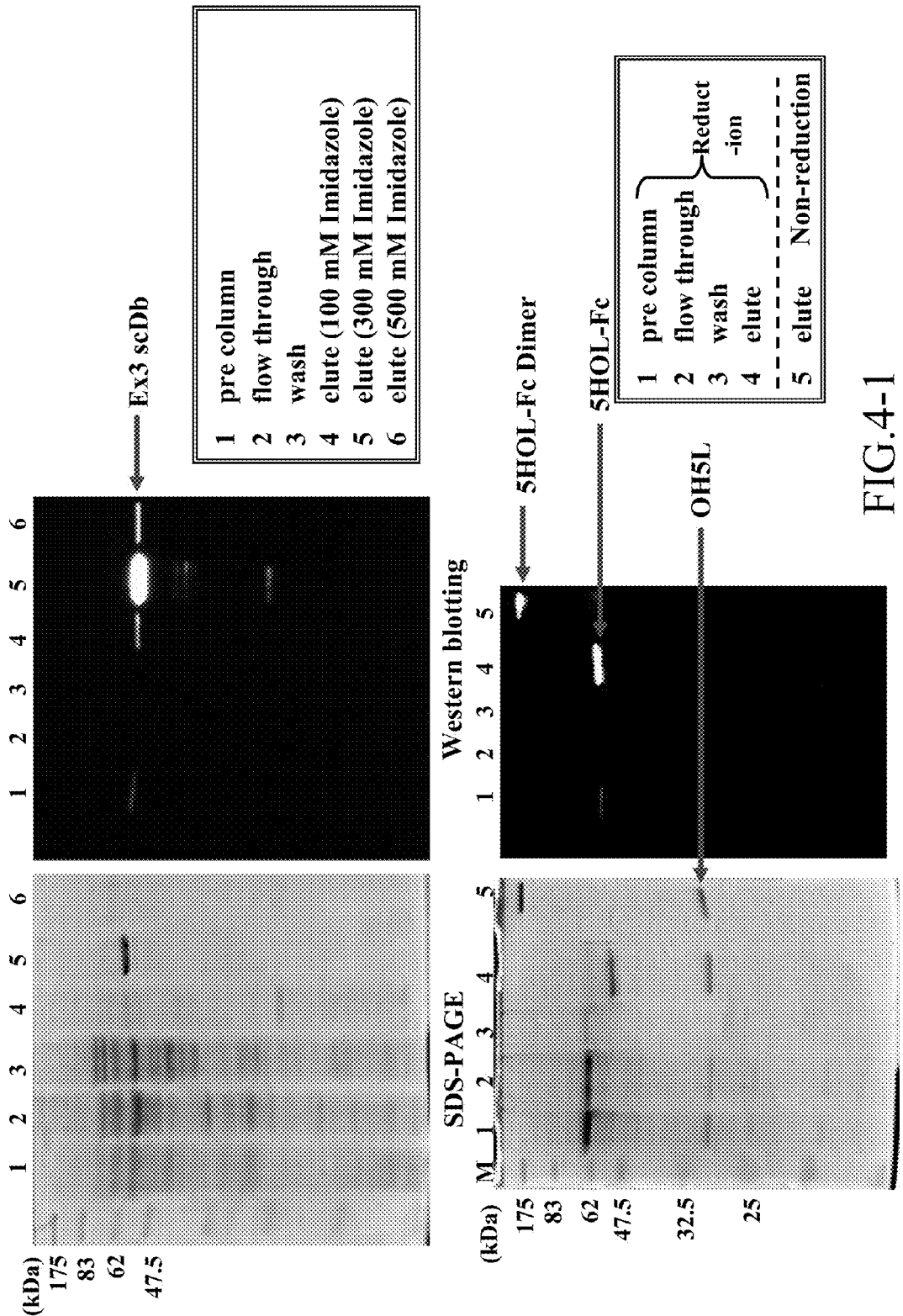
Figures 2, 4:
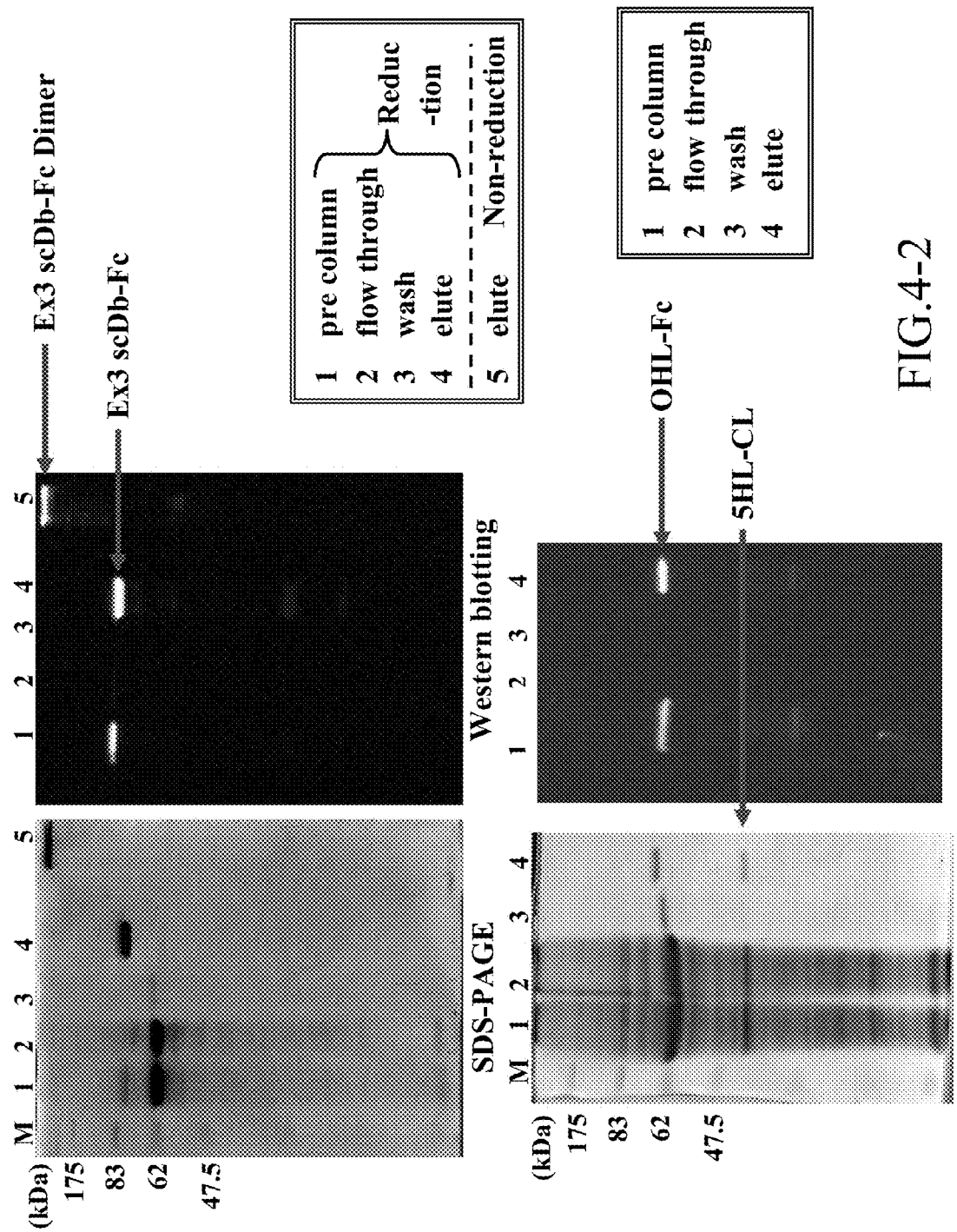

Representative examples of the amino acid sequences of the PreSission sequence, hinge region, peptide linker, signal peptide, etc. are shown in FIGS. 3-3 and 3-4. The PreSission sequence comprises a protease-cleavage site. There is no limitation on the kind of protease used in the present invention, and any enzyme known in the art such as Thrombin and Factor Xa may be used, and the amino acid sequence comprising the protease-cleavage site may be optionally selected.

The polypeptide having an amino acid sequence in which one or a few amino acids are substituted, deleted, inserted or added in the amino acid sequences represented by the above SEQ ID Nos, and having substantially the same property and function as that of the original polypeptide such as an antigen specificity as that of its variable region may be also used as a polypeptide constituting the present BsAb. it is preferale to make a substitution among amino acids belonging to the same group (polar, non-polar, hydrophobic, hydrophilic, positive-charged, negative-charged, or aromatic amino acid group), or to make a deletion or addition of amino acid so as not to cause a substantial difference or effects with respect to the three-dimensional or local charge-condition of the protein. Such polypeptides having the substitution, deletion or addition of the amino acid(s) my be easily prepared by well known methods such as site-specific mutation (point mutation method or cassette mutation), genetic homologous recombination, primer extension method and PCR, or any optional combinations thereof. The above amino acid sequence comprising one or few amino acids that are substituted, deleted, inserted or added have homology (identity) of 90% or more, preferably 95% or more, more preferably 99% or more with a full-length amino acid sequence in the original amino acid sequence.

The representative examples of the nucleic acid molecules (oligonucleotides) encoding the whole or part of the amino acid sequences of the single-chain polypeptide constituting the present BsAb have the nucleotide sequences shown in the above SEQ ID Nos. Furthermore, as a nucleic acid molecule with the nucleotide sequence having homology of 90% or more, preferably 95% or more, more preferably 99% or more with a full-length nucleotide sequence represented by the same SEQ ID Nos are considered to encode a polypeptide having substantially the same property and function as that of the original polypeptide or part thereof, the above nucleic acid molecule is included in the nucleic acid molecule of the present invention.

In order to determine the homology between two amino acid or nucleotide sequences, they may be preliminarily treated into an optimum condition for comparison. For example, a gap may be inserted into one of the sequences to optimize the alignment with the other sequence, followed by the comparison of amino acid or nucleotide at each site. When the same amino acid or nucleotide exists at a corresponding site of the first and second sequences, these two sequences are considered to be identical with respect to said site. Homology between two sequences is shown by a percent ratio of the number of the identical sites over the total number of amino acids or nucleotides between the two sequences.

The term "homology" in this specification means an amount (or a number) of the amino acids in an amino acid sequence or the nucleotides in a nucleotide sequence, which are determined to be identical with each other in the relationship between two sequences, showing an extent of the correlation between the two polypeptide or nucleotide sequences. The homology may be easily calculated. The term "homology" or "identity" is well known in the art, and many methods for the calculation of such homology are known, among them. For example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. &

Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991). A general method for the determination of the homology between two sequences is disclosed, for example, in Martin, J. Bishop (Ed.), Guide to Huge Computers, Academic Press, San Diego, (1994); Carillo, H. & Lipman, D., SIAM J. Applied Math., 48: 1073 (1988). A preferable method for the determination of the homology between two sequences is, for example, one designed to obtain a largely related part between said two sequences. Some of them are provided as a computer program. Preferable examples of the computer programs for the determination of the homology between two sequences include GCG program package (Devereux, J. et al., Nucleic Acids Research, 12(1): 387 (1984)), BLASTP, BLASTN, FASTA (Atschul, S. F. et al., J. Molec. Biol., 215: 403 (1990).

The nucleic acid of the present invention further includes a DNA molecule that hybridizes with a DNA comprising a nucleotide sequence complementary to the nucleotide sequence represented by the above SEQ ID Nos under stringent conditions, and encodes a polypeptide having substantially the same property and function as that of the polypeptides represented by the above SEQ ID Nos.

Hybridization may be carried out by or in accordance with a method well known in the art such as that described in Molecular cloning third. ed. (cold Spring Harbor Lab. Press, 2001). Hybridization may be done in accordance with an instruction or manual attached to a commercially available library.

Hybridization may be carried out by or in accordance with a method well known in the art such as that described in Current protocols in molecular biology edited by Frederick M. Ausbel et al., 1987). Hybridization may be done in accordance with an instruction or manual attached to a commercially available library.

The phrase "stringent conditions" in this specification may be defined by a suitable combination of salt concentration, organic solvent (for example, formamide), temperature, and other known conditions. Thus, stringency will be increased by the decrease of salt concentration, or the increase of an organic solvent concentration or hybridization temperature. The washing conditions after the hybridization may also affect the stringency. The washing conditions are also defined by salt concentration and temperature. The stringency of washing will be increased by the decrease of salt concentration or the increase of temperature.

Accordingly, the "stringent conditions" in this specification means conditions under which a specific hybrid can be formed only between the nucleotide sequences having homology of about 80% or more, preferably about 90% or more, more preferably about 99% or more on a total average. Specifically, they may be sodium concentration of 150-900 mM, preferably 600-900 mM, pH6-8 at 60-68° C. One example of the stringent conditions is hybridization in 5×SSC (750 mM NaCl, 75 mM Na$_3$ Citirate), 1% SDS, 5×Denhart solution 50% formaldehyde at 42° C., followed by the washing with 0.1×SSC (15 mM NaCl, 1.5 mM Na$_3$ Citirate), 0.1% SDS at 55° C.

The expression vectors used in the production of the single-chain polypeptide constituting the six types of the present BsAb may be easily prepared in accordance with known technologies in the art such as those described in Patent Document 1, for examples, in Examples 1, 2, 11 and 12, which concern the production of the diabody-type bispecific antibodies. All of the variable regions comprised in the expression vectors such as 5HOL, OH5L, 5HL (528 scFv), OHL (OKT3 scFv), OH-Fc (the Fc region of the humanized OKT3 antibody) and OL-CL (the light chain of the humanized OKT3 antibody) in the examples of the present specification are humanized in accordance with the method described in Patent Document 1. The constant region constituting the humanized OKT3 antibody, CH1, CH2, CH3 and CL are derived from the human IgG antibody The term "humanized antibody" as used herein means a human immunoglobulin (a recipient antibody) in which at least part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in the recipient antibody or the introduced CDR or framework. These changes are made in order to optimize or improve the properties of the resulting antibody. More detailed information on these changes are referred to Jones et al., Nature 321, 522-525 (1986); Reichmann et al., Nature 332, 323-329 (1988); EP-B-239400; Presta, Curr. Op. Struct. Biol 2, 593-596 (1992); and EP-B-451216.

The humanized variable region of the antibody may be prepared in accordance with any methods known to those skilled in the art, for example, by analyzing various conceptual humanized preparations based on three-dimensional immunoglobulin models of the recipient antibody and donor antibody, and analyzing them. The three-dimensional immunoglobulin models are well known in the art, being referred to, for example, WO92/22653.

Thus, one example of the humanized variable region according to the present invention is an antibody wherein the complementary determining regions (CDR) in the variable regions are derived from a mouse antibody, and the other parts are derived from a human antibody.

The activity or function of the resulting antibody may be deteriorated due to the humanization. The activity or function of the diabody-type bispecific antibody according to the present invention may be therefore improved by being provided with a site-specific mutation at an appropriate position in the single-chain polypeptide, for example, at a position in the framework which can affect the CDR structure, such as in canonical sequence or vernier sequence.

Each single chain polypeptide constituting the present BsAb may further optionally contain bacterial enterotoxin such as *staphylococcus enterotoxin, E. coli* enterotoxin, cholera enterotoxin, and their derivatives. However, it is well known that these super antigens may possibly cause cytokine-depending toxin shock syndromes due to their strong affinity towards MHC class II. Furthermore, various peptide tags (c-myc and His-tag, for example) known in the art may be contained at its end, etc.

In accordance with a method known to those skilled in the art, a nucleic acid encoding the single-chain polypeptide or each region contained therein may be obtained, and its nucleotide sequence may be determined, by using, for example, an oligonucleotide probe specifically binding to a gene encoding the heavy and light chains of the mouse antibody (R. Orlandi et al., Proc. Natl. Acad. Sci., USA 86: (1993)). The hybridomas producing the above monoclonal antibodies may be used as DNA source in these methods.

More specifically, the nucleic acid encoding the single-chain polypeptide may be prepared by replacing VH or VL in a single-chain Fv (or "scFv") already constructed and known in the art or in a known diabody-type bispecific antibody with another VH or VL derived from another antibody having a different specificity. The term "scFv" as used herein means a single-chain polypeptide having VH domain and VL domain of an antibody within a single-chain polypeptide. Usually the scFv polypeptide has a linker between the two domains in order to give a structure necessary for showing antigen-binding activity. Rosenburg and Moore (Ed.), "The Pharmacology of Monoclonal Antibodies," Vol. 113, Springer-Verlag, New York pp. 269-315 (1994) may be referred to with respect to scFv.

Furthermore, the nucleic acid encoding the humanized variable regions in the single-chain polypeptide of the present invention may be synthesized by means of an over-lapping PCR method based on a pre-determined amino acid sequence. The nucleic acid used herein has no limitation in its chemical structure or preparation route, as long as it is a molecule encoding the single-chain polypeptide, including gDNA, cDNA chemically-synthesized DNA and mRNA.

Specifically, the nucleic acid according to the present invention may be isolated from cDNA library by means of hybridization or PCR based on the sequences disclosed in literatures. The thus isolated DNA may be inserted in an expression vector, with which a host cell such E. coli, COS cell, CHO cell or myeloma not expressing immunoglobulin are transfected to synthesize a monoclonal antibody in the thus transformed host cells. PCR may be carried out in accordance with a method known in the art, or substantially the same or altered methods. The methods disclosed in, for example, R. Saiki, et al., Science, 230:1350, 1985; R. Saiki, et al., Science, 239:487, 1988; H. A. Erlich ed., PCR Technology, Stockton Press, 1989; D. M. Glover et al., ed., "DNA Cloning," $2^{nd}$. ed., Vol. 1, (The Practical Approach Series), IRL Press, Oxford University Press (1995); M. A. Innis et al., ed., "PCR Protocols: a guide to methods and applications," Academic Press, New York (1990); M. J. McPherson, P. Quirke and G. R. Taylor (Ed.), PCR: a practical approach, IRL Press, Oxford (1991); M. A. Frohman et al., Proc. Natl. Acad. Sci. USA, 85, 8998-9002 (1988), and their modified and altered methods may be used in the present invention. PCR may be performed with use of a commercially available kit in accordance with manufacturer's protocols.

Hybridization may be referred to L. Grossman et al. (ed.), "Methods in Enzymology", Vol. 29 (Nucleic Acids and Protein Synthesis, Part E), Academic Press, New York (1974). The sequencing method of nucleic acids such as DNA may be referred to Sanger et al., Proc. Natl. Acad. Sci. USA 74:5463-5467 (1977). A general method for recombinant DNA techniques may be referred to J. Sambrook, E. F. Fritsch & T. Maniatis (ed.), "Molecular Cloning: A Laboratory Manual (2nd edition)", Cold Spring Harbor Laboratory Press, Cold Spring Harbor, N.Y. (1989) and D. M. Glover et al. (ed.), 2nd ed., Vol. 1 to 4 (The Practical Approach Series), IRL Press, Oxford University Press (1995).

The nucleic acid encoding the single-chain polypeptide constituting the present BsAb or each region contained therein may be modified or altered so that it will optionally encode a desired peptide or amino acid depending on the purpose. The techniques for such modification or alternation are disclosed in Mutagenesis: a Practical Approach, M. J. McPherson (ed.), IRL Press, Oxford, UK (1991), including a site-specific mutagenesis introduction method, cassette mutagenesis induction method and PCR mutagenesis method.

The term "modification (or alternation)" as used herein refers to insertion, deletion or substitution of base(s) in at least one codon encoding an amino acid residue in the originally obtained nucleic acid. It includes alternation of the amino acid sequence per se of the single-chain polypeptide by replacing a codon encoding the original amino acid with a codon encoding another amino acid. The single-chain polypeptide constituting the present BsAb may be obtained in this way.

Alternatively, the nucleic acid encoding the single-chain polypeptide may be altered without changing the amino acid per se, by using a codon suitable for a host cell (an optimum codon). With the use of the optimum codon, expression efficiency of the single-chain polypeptide in the host cell will be improved.

The linker and super antigen may be optionally introduced into the single-chain polypeptide constituting the present BsAb by means of any techniques well known in the art such as genetic engineering technique including recombinant technology and chemical synthesis of peptides.

The single-chain polypeptide may be produced by various methods well known in the art such as genetic engineering technique and chemical synthesis. The genetic engineering technique includes constructing a replicable cloning vector or expression vector, transforming the host cell with the vector, culturing the transformed host cell to express the nucleic acid in it, collecting and purifying the single-chain polypeptide. The vector usually comprises the nucleic acid encoding one of the two single-chain polypeptides constituting the present BsAb. In such case, the resulting two kinds of the vectors are preferably introduced into the same host cell. Alternatively, the two kinds of nucleic acid encoding the different single-chin polypeptide from each other may be comprised in the same vector.

The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which can not be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell.

Any cell known in the art may be used as the host cell, for example, there may be mentioned procaryotic cells such as including E. coli., eucaryotic cells such as mammalian cells such Chinese hamster ovary (CHO) cell and human cells, yeast, and insect cells.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such ethanol, a dissolving agent such as guanidine hydrochloride and urea.

The present BsAb is produced by assembling the two kinds of the single-chain polypeptides thus purified, and separating and collecting the thus formed antibody molecule.

Assembling treatment will bring a single-chain polypeptide back in its appropriate spatial arrangement in which a desired biological activity is shown. Since this treatment may also bring polypeptides or domains back into their assembling state, it may be considered "re-assembling." It may be also called "re-constitution" or "refolding" in view of gaining the desired biological activity. The assembling treatment may be carried out by any method known in the art, preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the present BsAb thus formed may be done by any method known in the art as well.

A pharmaceutical preparation according to the present invention comprises an active ingredient selected from the group consisting of the present BsAb, the single-chain polypeptide, the nucleic acid, the vector, and the host cell described in the above. As shown by the examples in the present specification, since the active ingredient has an activity of eliminating, hurting, damaging and/or reducing tumor cells expressing EGFR in vitro and in vivo, the present pharmaceutical preparation is used as an anti-tumor agent.

Furthermore, it is demonstrated by the examples in the present specification that co-existence of the present BsAb with the tumor cells expressing human EGFR and the cells having phagocytosis or cytotoxic activity in vitro or in vivo will increase the production of cytokines such as IFN-γ, GM-CSF, and TNF-α by the cells having phagocytosis or cytotoxic activity. The pharmaceutical preparation according to the present invention may be therefore used for the above purposes as well. In vitro, for example, the addition of the present BsAb to a culture system comprising the above two kinds of the cells will increase the production of the cytokines.

An effective amount of the active ingredient may be optionally determined by those skilled in the art depending on the purpose of treatment, medical conditions of a patient to be treated such as kind, site or size of tumor, and administration route. A typical dose or daily dose may be first determined in vitro by using an assay method of growth or existence of the tumors known in the art, then determined with use of such an appropriate animal model as to allow extrapolation of the resulting dose range to human patients.

The pharmaceutical preparation of the present invention may optionally comprise various kinds of pharmaceutically acceptable components known in the art such as carrier, excipient, buffer, stabilizing agent and the like, depending on various factors such as the kind of the active ingredients, its formulation form, the route and purpose of administration, medical conditions of patient.

The pharmaceutical preparation of the present invention may be formulated into any form such as pill, liquid, powder, gel, air spray, microcapsule, and colloidal dispersion (liposome, micro emulsion, etc.).

The pharmaceutical preparation may be administered by injecting or infusing intraveneously, intraperitoneally, intracerebrally, intraspinally, intramuscularly, intraocularly, intraarterially, especially intrabiriarily, or via diseased tissue, or with use of a constant releasing agent system. The active ingredient according to the present invention may be administered through continuous fluid infusion or massive injection. The pharmaceutical preparation according to the present invention is preferably administered in combination with the cell having phagocytosis or cytotoxic activity. Alternatively, the active ingredient such as the present BsAb may be mixed with the above cells so as to bind to them before its administration.

The constant releasing agent generally refers to a formulation that can release the active ingredient of the present invention for a certain period of time. One of the preferred constant releasing agents comprises a semi-permeable carrier of solid hydrophobic polymer such as protein, which is shaped into a form such as film or micro capsule.

The pharmaceutical preparation according to the present invention may be produced by a method that is optionally selected from, for example, "Guide Book of Japanese Pharmacopoeia", Ed. of Editorial Committee of Japanese Pharmacopoeia, Version No. 13, published Jul. 10, 1996 by Hirokawa publishing company The terms as used in the present specification and drawings are based on IUPAC-IUB Commission on Biochemical Nomenclature or on meanings of the terms conventionally used in the art.

The present invention will be explained more in detail by referring to the Examples, which are provided only for describing the specific embodiments of the present invention, but not for limiting the scope of the present invention. It is therefore to be understood that various embodiments based on the inventive concept of the present specification may be practiced within the scope of the present invention.

The following examples were or can be carried out with standard techniques well known to those skilled in the art unless otherwise described. Thus, unless otherwise described, specific procedures and treating conditions are in accordance with J. Sambrook, E. F. Fritsch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to 4, (The Practical Approach Series), IRL Press, Oxford University Press (1995) (DNA cloning), and with H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990) (PCR). A commercially available agent and kit were used in accordance with protocols attached thereto.

REFERENCE EXAMPLE 1

Cloning of Anti-Epidermal Growth Factor Receptor Antibody

Mouse B cell hybridoma 528 producing anti-EGFR antibody (ID:TKG0555) was provided by Cell Resource Center for Biomedical Research, Institute of Development, Aging and Cancer, TOHOKU University. mRNA was extracted with ISOGEN (Nippon Gene Co.) and then cDNA was prepared by means of First-Strand cDNA Synthesis Kit (Amersham Biosciences Co.). PCR reaction was done for the cDNA using cloning primers that were synthesized based on Reference 1 to determine the sequences of variable regions of 528, VH (referred to as "5H") and VL (referred to as "5L"). The above hybridoma 528 producing anti-EGFR antibody is also stored at ATCC with an ATCC Accession No. HB-8509, and is therefore obtainable from the same depository.

Reference 1: Krebber, A. et al. Reliable cloning of functional antibody variable domains from hybridomas and spleen cell repertoires employing a reengineered phage display system. J Immunol Methods 201, 35-55. (1997).

REFERENCE EXAMPLE 2

Preparation of Ex3 Diabody-Expressing Vector

The diabody-type bispecific antibody, Ex3 diabody (referred to as "Ex3"), consists of two molecules, i.e., "5HOL" and "OH5L." The expression vector was prepared based on the expression vector for Mx3 diabody (referred to as "Mx3") that was already constructed by the inventors and has specificity to MUC1 and CD3 (PCT Publication No. WO02/06486). Thus, "5H" was amplified with PCR using A-B primers comprising a restriction enzyme site, digested with NcoI-EagI, and was replaced with "MH" in pSNE4-MHOL (VH of anti-MUC1 antibody (MUSE11) (referred to as "MH")-GGGGS (referred to as "G1")-VL of anti-CD3 antibody OKT3 (referred to as "OL") to give pRA-5HOL. Similarly, "5L" was amplified with PCR using C-D primers comprising a restriction enzyme site, digested with EcoRV-SacII, and was replaced with "ML" in pSNE4-OHML (VH of OKT3 (referred to as "OH")-"G1"-VL of MUSE11 (referred to as "ML") to give pRA-OH5L. A c-myc peptide tag for detection and a His-tag (Hisx6:histidine-hexamer) for purification were introduced successively into the vectors. The anti-CD3 antibody, OKT3 (ID:TKG0235) was provided by Cell Resource Center for Biomedical Research, Institute of Development, Aging and Cancer, TOHOKU University, and is also stored at ATCC with an ATCC Accession No. CRL-8001, and is therefore obtainable from the same depository.

A NcoI-5H back primer
[SEQ ID No.1]
5'-nnnccatggcccaggtccagctgcagcagtctg-3'

B 5H-EagI forward primer
[SEQ ID No.2]
5'-nnncggccgaggagactgtgagagtggt-3'

C EcoRV-5L back primer
[SEQ ID No.3]
5'-nnngatatcctaatgacccaatctcc- 3'

D 5L-SacII forward primer
[SEQ ID No.4]
5'-nnnccgcggcacgtttgatttccagcttg- 3'

REFERENCE EXAMPLE 3

Preparation of Humanized Ex3 Gene

It was already reported that the variable region of the humanized OKT3 could maintain its activity when compared with the mouse OKT3 (Reference 2). The total gene was synthesized by means of overlapping PCR based on the amino acid sequence of the variable regions of the humanized OKT3 disclosed in the Reference 2. The optimum codons for E. coli were used in the synthesis. It was also reported that the use of the gene containing the optimum codons would increase the expression level in E. coli.

The humanization of the variable regions of 528 was performed by means of CDR grafting. Thus, a human antibody having FR (Frame Work) with the highest homology was screened and selected by a homology search in view of the length of each CDR and the like. An amino acid sequence was designed, in which the CDR of the selected human antibody was replaced with CDR of 528. The total gene was then synthesized by means of overlapping PCR by using the optimum codons for E. coli.

Reference 2: Adair, J. R. et al. Humanization of the murine anti-human CD3 monoclonal antibody OKT3. Hum Antibodies Hybridomas 5, 41-7. (1994).

REFERENCE EXAMPLE 4

Preparation of Expression Vector of Humanized Ex3

The humanized Ex3 diabody was made of the two molecules of h5HhOL and hOHh5L. The expression vectors were constructed based on the expression vectors constituting Ex3. Thus, the humanized 5H was amplified with PCR using E-F primers comprising a restriction enzyme site, digested by NcoI-EagI, and replaced with "5H" in pRA-5HOL. Then, the humanized OL was amplified with PCR using G-H primers comprising a restriction enzyme site, digested by EcoRV-SacII, and replaced with "OL" in pRA-5HOL to finally give a humanized pRA-5HOL. Similarly, the humanized OH was amplified with PCR using I-J primers comprising a restriction enzyme site, digested by NcoI-EagI, and replaced with "OH" in pRA-OH5L. Then, the humanized 5L was amplified with PCR using K-L primers comprising a restriction enzyme site, digested by EcoRV-SacII, and replaced with "5L" in pRA-OH5L to finally give a humanized pRA-OH5L. A c-myc peptide tag for detection and a His-tag (Hisx6:histidine-hexamer) for purification were introduced successively at C-end of the vector as in the vector expressing Ex3.

E NcoI-h5H back primer
[SEQ ID No.5]
5'-nnnccatggcccaggtgcaactggttcagagc-3'

F h5H-EagI forward primer
[SEQ ID No.6]
5'-nnncggccgagctcacggtaaccagcgta-3'

G EcoRV-hOL back primer
[SEQ ID No.7]
5'-nnngatatccagatgacccagag-3'

H hOL-SacII forward primer
[SEQ ID No.8]
5'-nnnccgcggcgcgggtaatctgc-3'

I NcoI-hOH back primer
[SEQ ID No.9]
5'-nnnccatggcccaggtgcaactggtg-3'

J hOH-EagI forward primer
[SEQ ID No.10]
5'-nnncggccgagctaacggtcacc-3'

K EcoRV-h5L back primer
[SEQ ID No.11]
5'-nnngatatcgtgatgacccagagccc-3'

L h5L-SacII forward primer
[SEQ ID No.12]
5'-nnnccgcggcgcgtttaatttccactttggtgccac-3'

EXAMPLE 1

Figure 2:
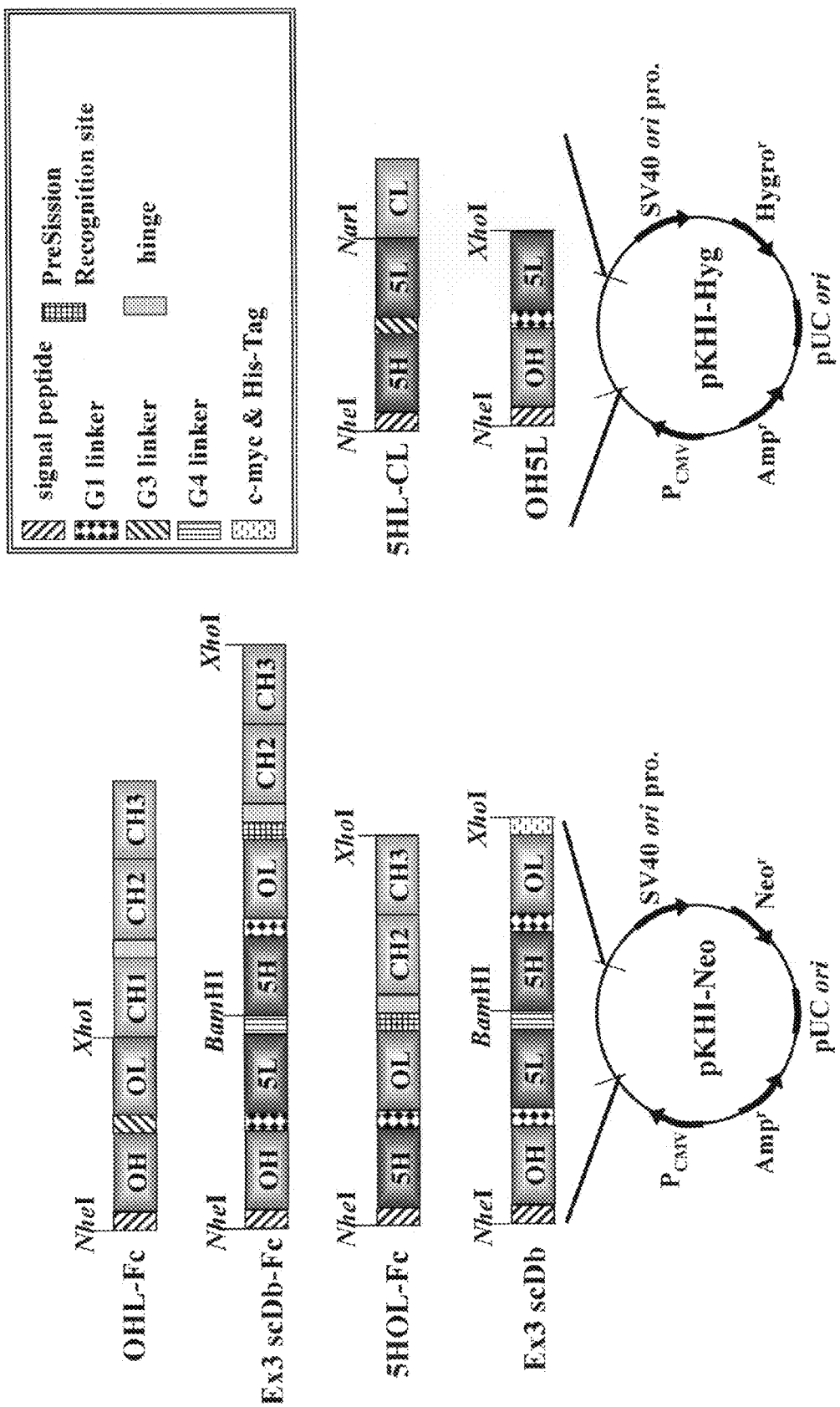
FIG. 2 is a schematic figure showing an expression vector encoding a polypeptide constituting the humanized highly functional bispecific antibody.

Preparation of Expression Vector of the Present BsAb (FIG. 1 and FIG. 2)

(1) The First Type

The humanized 5HOL (referred to hereinafter just as "5HOL") was amplified with PCR using a-b primers comprising a restriction enzyme site, digested by BamHI-XhoI, and inserted into the animal cell expression vector pKHI-Neo. The humanized OH5L (referred to hereinafter just as "OH5L") was amplified with PCR using c-d primers and with $2^{nd}$ PCR using e-f primers, digested by NheI-BamHI, and inserted into the upstream of 5HOL to give pKHI-Ex3 scDb. A c-myc peptide tag for detection and a His-tag (Hisx6: histidine-hexamer) for purification were introduced successively at C-end of the vector.

(2) The Second Type

As Ex3-Fc consists of OH5L and 5HOL-Fc, only the latter was newly prepared. 5HOL and OH-Fc were amplified with PCR using g-h primers and i-j primers, respectively. The resulting PCR products were mixed and amplified with PCR using e-j primers, digested by NheI-XhoI, and replaced with Ex3 scDb of pKHI-Ex3 scDb to give pKHI-5HOL-Fc.

(3) The Third Type

5HOL-Fc was amplified with PCR using a-j primers, digested by BamHI-XhoI and replaced with 5HOL of pKHI-Ex3 scDb to give pKHI-Ex3 scDb-Fc. Both Ex3-Fc and Ex3 scDb-Fc have the PreSission protease cleavage site upstream of Fc.

(4) The Fourth Type

Ex3 scFv-Fc consists of OHL-FC and 5HL-CL. OHL was amplified with PCR using c-k primers and with 2nd PCR using e-k primers, digested by NheI-XhoI and replaced with OH of pKHI-OH-Fc to give pKHI-OHL-Fc. On the other hand, 5HL was amplified with PCR using g-1 primers and with 2nd PCR using e-1 primers, digested by NheI-NarI and replaced with OL of PKHI-OL-CL to give pKHI-5HL-CL. The pKHI-Neo and pKHI-Hyg vectors were prepared by inserting a secretion signal for the expression in an animal cell and Kozak sequence for increasing the transcription rate into a multicloning site of pcDNA3.1-Neo and pcDNA3.1-Hyg (Invitrogen Co.), respectively.

a G2 linker-528H back primer:
[SEQ ID No.13]
5'-ggcggcggcggctccggtggtggtggatcccaggtgcaactggttcagagc-3' b c-myc & His-tag-XhoI forward primer:
[SEQ ID No.14]
5'-nnncggccgaggagactgtgagagtggt-3' c signal H-OH back primer:
[SEQ ID No.15]
5'-gtaactgcaggtgtccactcccaggtgcaactggtgcagag-3' d 5L-G3 linker forward primer:
[SEQ ID No.16]
5'-ggagccgccgccgccagaaccaccaccaccagaaccaccaccacctg cagccgcggcgcgtttaatttccactttggt-3' e NheI-signal H back primer:
[SEQ ID No.17]
5'-nnngctagccaccatggattgggtgtggaccttgctattcctgttgt cagtaactgcaggtgtccactcc-3' f G4 linker-BamHI forward primer:
[SEQ ID No.18]
5'-nnnggatccaccaccaccggagccgccgccgccagaacc-3' g signal H-5H back primer:
[SEQ ID No.19]
5'-gtaactgcaggtgtccactcccaggtgcaactggttcagag-3' h OL-precission forward primer:
[SEQ ID No.20]
5'-cccctggaacagaacttccagggcgcgggtaatctgcagttt-3' i PreSission-hinge back primer:
[SEQ ID No.21]
5'-ctggaagttctgttccaggggcccgacaaaactcacacatgc-3' j CH3-XhoI forward primer:
[SEQ ID No.22]
5'-nnnctcgagtcatttacccggagacagggagag-3' k hOL-XhoI forward primer:
[SEQ ID No.23]
5'-nnnctcgagcgggtaatctgcagtttggta-3' l h528L-NarI forward primer:
[SEQ ID No.24]
5'-nnnggcgccgccacagtgcgtttaatttccactttggtgcc-3'

EXAMPLE 2

Preparation of the Four Kinds of BsAb Using Animal Cells

Ex3 scDb: The expression vector pKHI-Ex3 scDb was introduced into a CHO cell, screened in an antibiotic-selection medium comprising G418 and subjected to a limiting dilution, so that a stably expressing strain was cloned with a cytotoxicity test (MTS Assay) and flow cytometry. After the cloned strain was cultured in a serum-free medium in a roller bottle, the resulting culture supernatant was dialyzed against PBS and purified with a metal-chelating affinity chromatography (IMAC). The purification was confirmed with SDS-Polyacrylamide gel electrophoresis (SDS-PAGE) and Western blotting (FIG. 4-1).

Ex3-Fc: The expression vector pKHI-OH5L and pKHI-5HOL-Fc were co-introduced into the CHO cell and screened in an antibiotic-selection medium comprising G418 and Hygromycin. The cloning was carried out in the same way, and purified with Protein A affinity column chromatography (FIG. 4-1).

Ex3 scDb-Fc: The expression vector pKHI-Ex3 scDb-Fc was introduced into the CHO cell, screened in the antibiotic-selection medium comprising G418, and purified in the same way as Ex3-Fc (FIG. 4-2).

Ex3 scFv-Fc: The expression vector pKHI-OHL-Fc and pKHI-5HL-CL were co-introduced into the CHO cell, screened in the antibiotic-selection medium comprising G418 and Hygromycin and purified in the same way as Ex3-Fc (FIG. 4-2).

It was observed that desired molecules were prepared with a high purification degree. A yield of each molecule after the purification was about 1 mg per 1 L of the culture medium.

EXAMPLE 3

Figure 5:
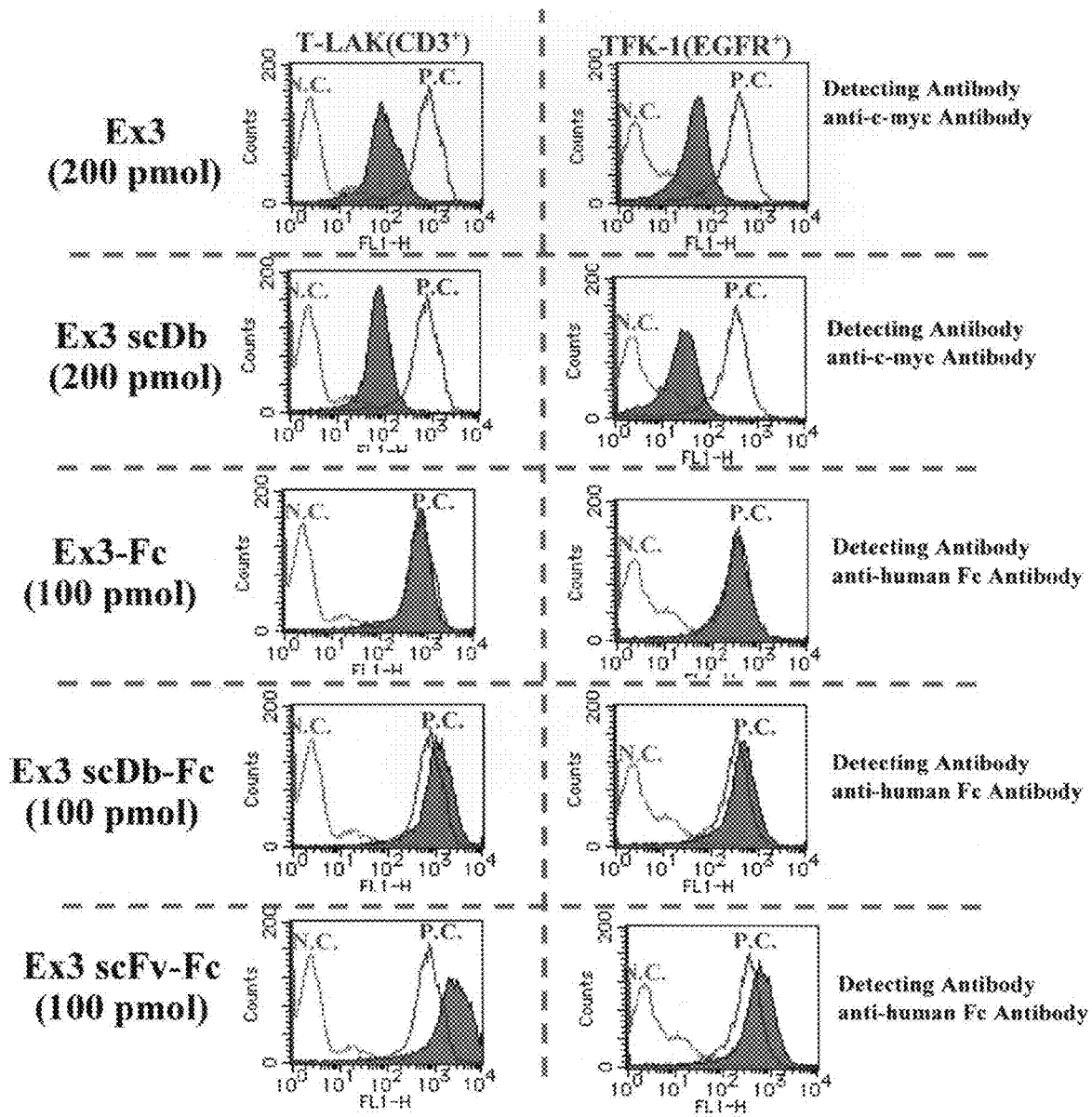
FIG. 5 shows the results of binding test with Flow Cytometry.

Evaluation (1) of the Function of the Four Kinds of the Present BsAb—Flow Cytometric Analysis The binding activity of the four kinds of the present BsAb and Ex3 to various cells was examined with Flow cytometry. Target cells were mixed with a first antibody of Ex3, Ex3 scDb of 200 pmol, and the other BsAbs of 100 pmol, left to stand still for 30 min. at 4° C., washed twice with 0.1% $NaN_3$/PBS, mixed with a second antibody of anti-c-myc antibody or anti-human Fc antibody, and finally mixed with a third antibody of FITC-labeled anti-mouse antibody followed by the same procedures, and subjected to the detection of fluorescence. For a negative control (NC), only the procedures after the addition of the second antibody were carried out. On the other hand, OKT3 IgG and 528 IgG were used as a positive control (referred to as "PC") for T-LAK cell and TFK-1 cell (human bile duct carcinoma cell line), respectively. The results showed that they could bind to both the cells (FIG. 5). The divalent BsAb according to the present invention showed such a binding activity as is comparable to or a little stronger than that of IgG (FIG. 5).

EXAMPLE 3

Figure 6:
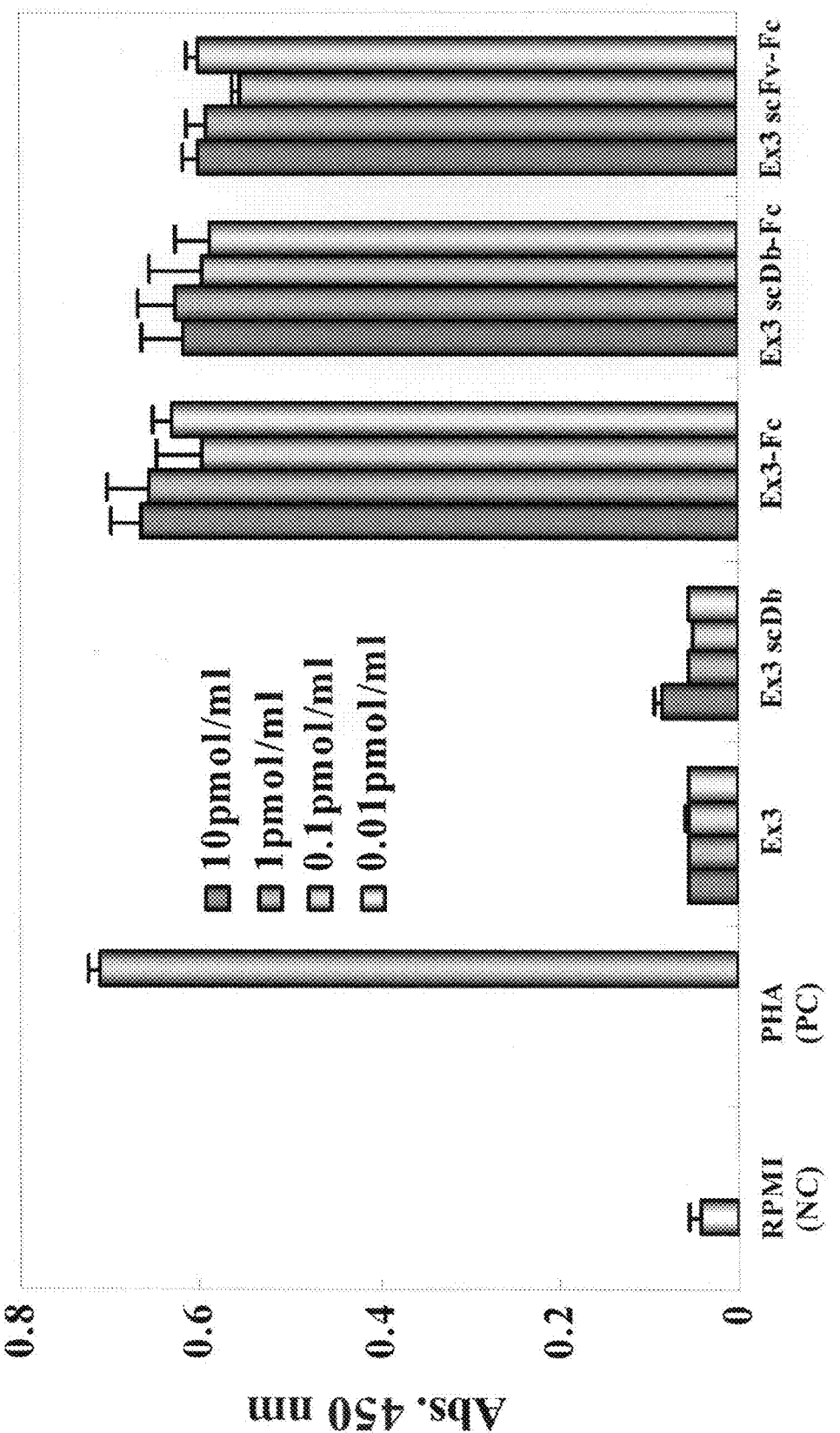
FIG. 6 shows the results of PBMC proliferation assay. Bars for each BsAb mean its added concentration of 10 pmol/ml, 1 pmol/ml, 0.1 pmol/ml and 0.01 pmol/ml, respectively, in the order of from the left to the right.

Evaluation (2) of the Function of the Four Kinds of the Present BsAb—PBMC Proliferation Assay Peripheral blood lymphocytes (PBMC) were placed in a 96-well plate at a concentration of $5×10^4$ cells/50 µl/well, mixed with each BsAb with an adjusted concentration and incubated for 48 hours at 37° C. PBMC proliferation was determined by incorporation of an added 5-bromodeoxyuridine (BrdU) with absorbance at 450 nm. The results showed that a strong growth activity for PBMC, which was comparable to that obtained by the addition of PHA of PC, was observed only with respect to Ex3-Fc, Ex3 scDb and Ex3 scFv-Fc that had the fused human Fc region. It is considered that the human Fc region bonded to the Fc receptor that was present in NK cells and the like comprised in PBMC to transmit an activating signal (FIG. 6).

EXAMPLE 3

Evaluation (3) of the Function of the Four Kinds of the Present BsAb—In Vitro Cytotoxicity Test (MTS Assay)

Figure 7:
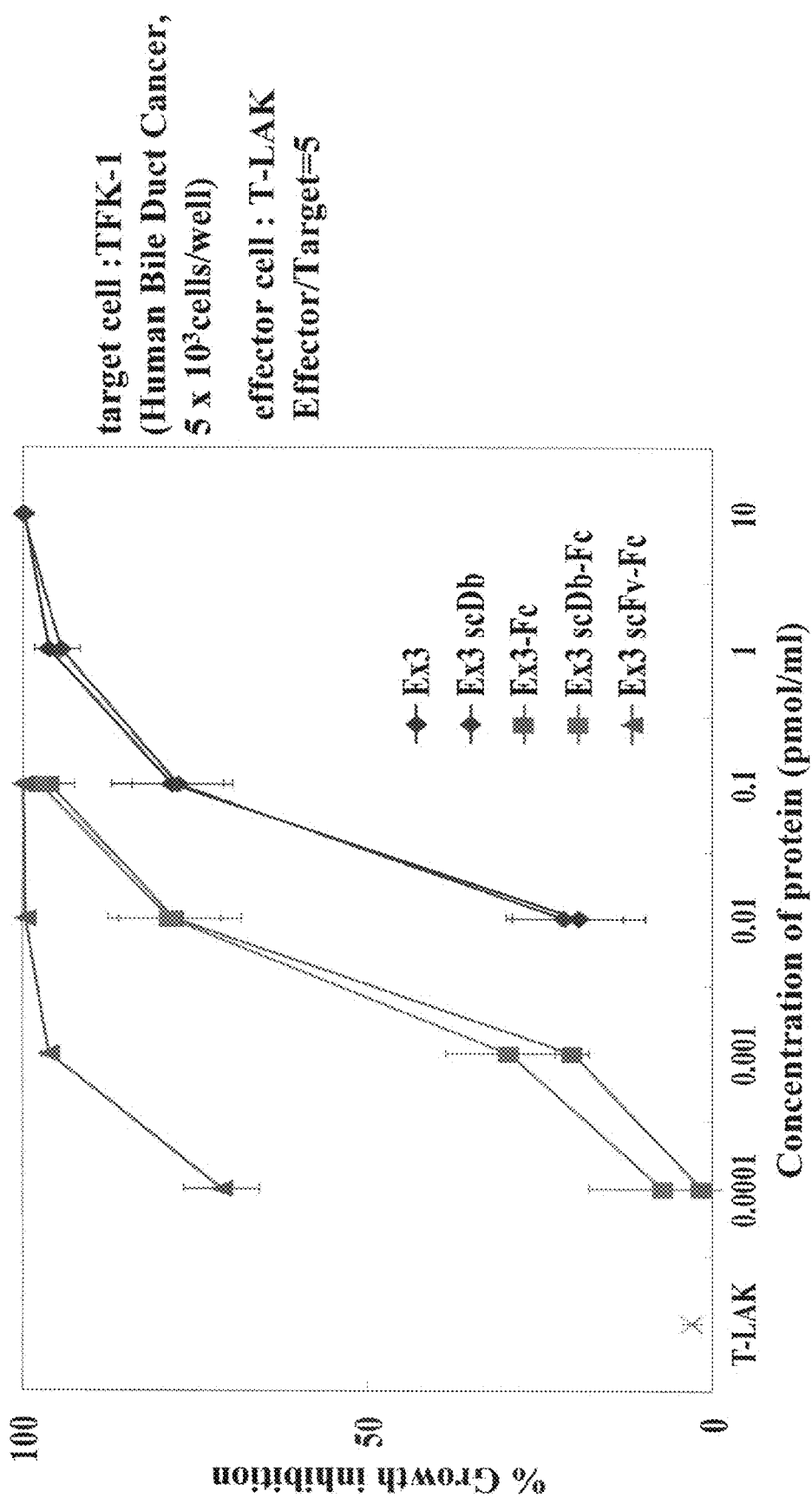
FIG. 7 shows the results of Cytotoxicity Test with use of T-LAK.

The degree of damage in TFK-1 cell given by T-LAK cell was determined by MTS assay. TFK-1 cell sample was adjusted by counting to contain $5×10^3$ cells per 100 µL of RPMI 1640, and its aliquot of 100 µL was dispensed into each well of a 96-well plate to stand still overnight at 37° C. After being diluted with RPMI to a desired concentration of the protein according to the present invention, 50 µL of which was put into each well of the above plate. LAK cell was diluted with RPMI to a desired E/T (Effector (T-LAK cell)/Target (TFK-1 cell)) ratio, and 50 µL of the protein solution was put into each well of the above plate as well. After being cultured for 48 hours at 37° C., the culture medium were removed. The cells were then washed with PBS, mixed with MTS (CellTiter 96 AQueous Non-Radioactive Cell Proliferation Assay, Promega Co.), PMS (CellTiter 96 AQueous Non-Radioactive Cell Proliferation Assay, Promega Co.), and RPMI, and incubated for 30-60 min. at 37° C., followed by the detection of absorbance at 490 nm with a plate reader. It was observed that Ex3 scDb showed the cytotoxicity similar to Ex3, depending on the concentration. On the other hand, Ex3-Fc and Ex3 scDb-Fc showed the cytotoxicity similar to and about ten times stronger cytotoxicity than Ex3, respectively. Ex3 scFv-Fc showed the cytotoxicity similar to Ex3 at about 1/1,000 times smaller concentration than Ex3 (FIG. 7).

MTS assay using PBMC showed that the cytotoxicity of Ex3 scDb was similar to Ex3, and that the cytotoxicity of Ex3-Fc, Ex3 scDb-Fc and Ex3 scFv-Fc were increased in this order (FIG. 8), giving us expectation of its single use for the clinical application.

Figure 9:
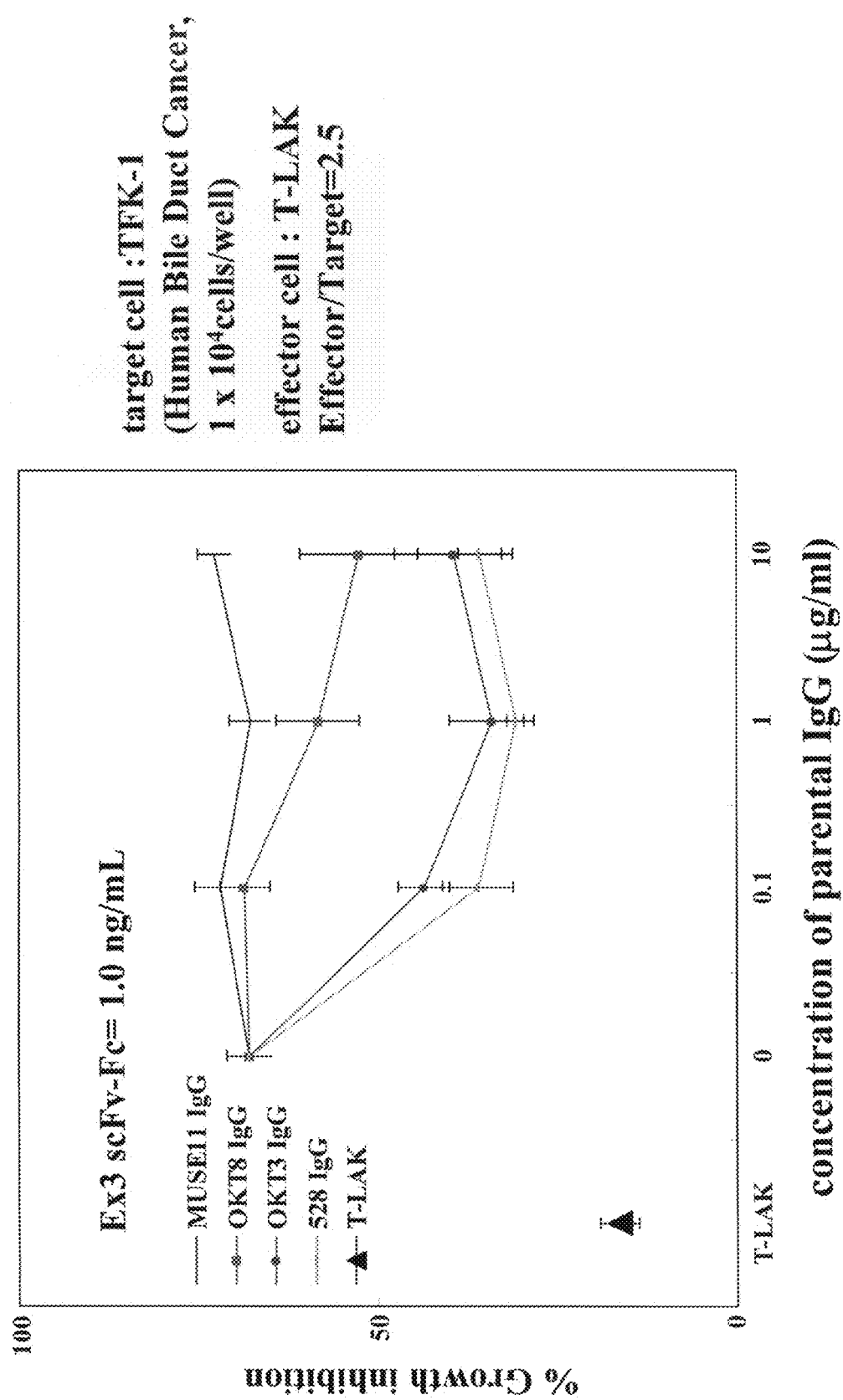
FIG. 9 shows the results of inhibition of Cytotoxicity by IgG.
Figure 10:
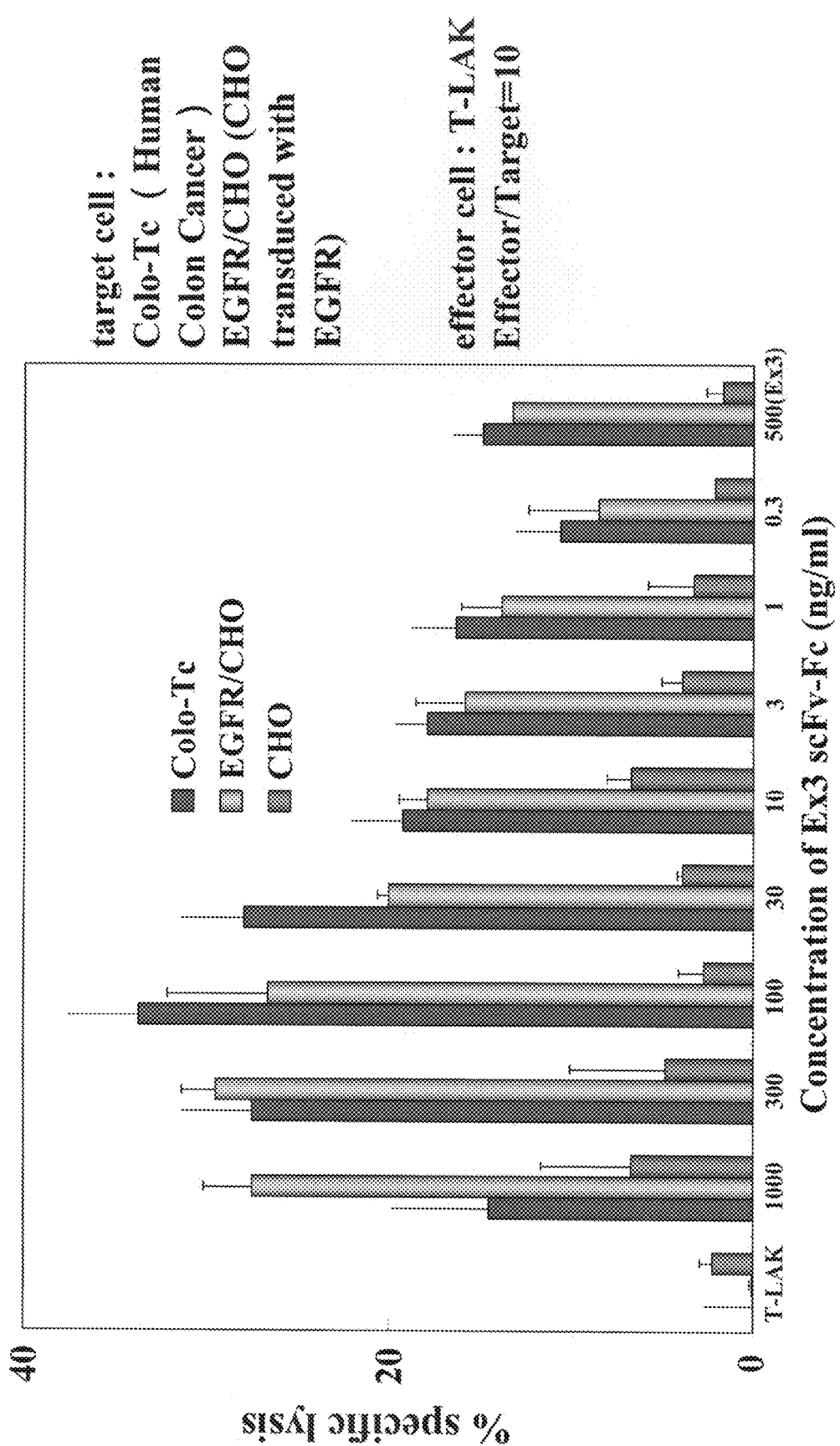
FIG. 10 shows an antigen-specific cytotoxicity of Ex3 scFv-Fc. Bars for each concentration of Ex3 scFv-Fc mean Colo-Tc, EGFRICHO and CHO in the order of from the left to the right.

In the inhibition test using Ex3 scFv-Fc by the addition of various IgG, while the parent antibodies, OKT3 and 528 IgG, showed a concentration-dependent decrease of cytotoxicity, no decrease was observed by the addition of non-relevant antibodies, OKT8 or MUSE11 IgG (FIG. 9).

EXAMPLE 6

Evaluation of the Function of Ex3 scFv-Fc—In Vitro Cytotoxicity Test ($^{51}$Cr Release Assay)

Although MTS assay could easily examine the cytotoxicity in vitro, it detected only growth inhibition of the attached cancer cells. $^{51}$Cr release assay was then carried out, which could detect directly the cytotoxicity. The results showed a significant cytotoxicity due to the addition of Ex3 scFv-Fc, depending on its concentration and antigen, which was comparable to that of Ex3 at about 1/500 smaller concentration than Ex3.

EXAMPLE 7

Preparation of Two Molecules of Ex3 and, Ex3 scDb from Ex3-Fc and Ex3 scDb-Fc

Figure 11:
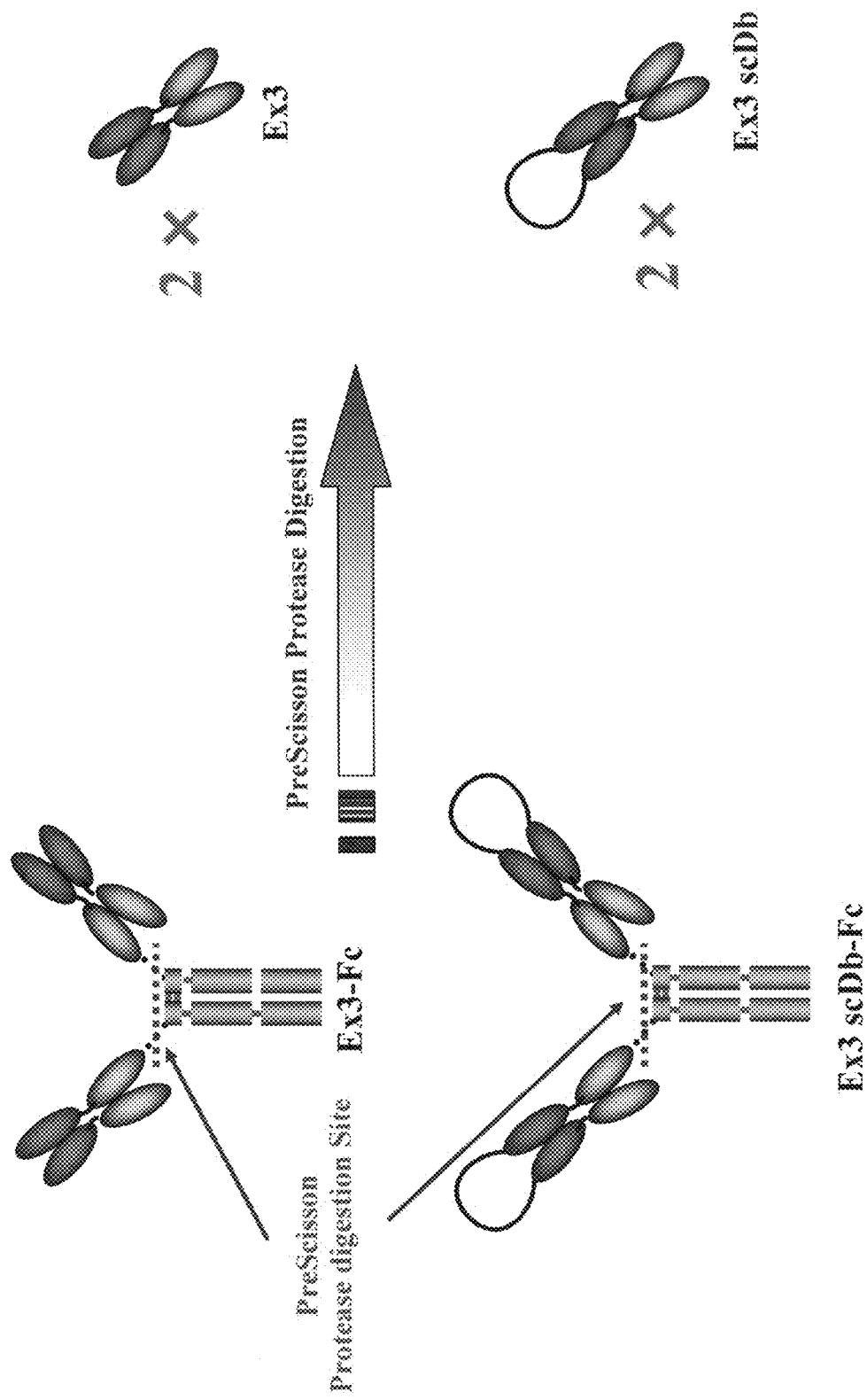
FIG. 11 is a schematic figure showing the preparation of two molecules of Ex3 and Ex3 scDb from Ex3-Fc and Ex3 scDb-Fc.

Ex3-Fc and Ex3 scDb-Fc were designed to give two molecules of each of Ex3 and Ex3 scDb by removal of the Fc region by PreSission protease digestion (FIG. 1 and FIG. 11).

Figure 12:
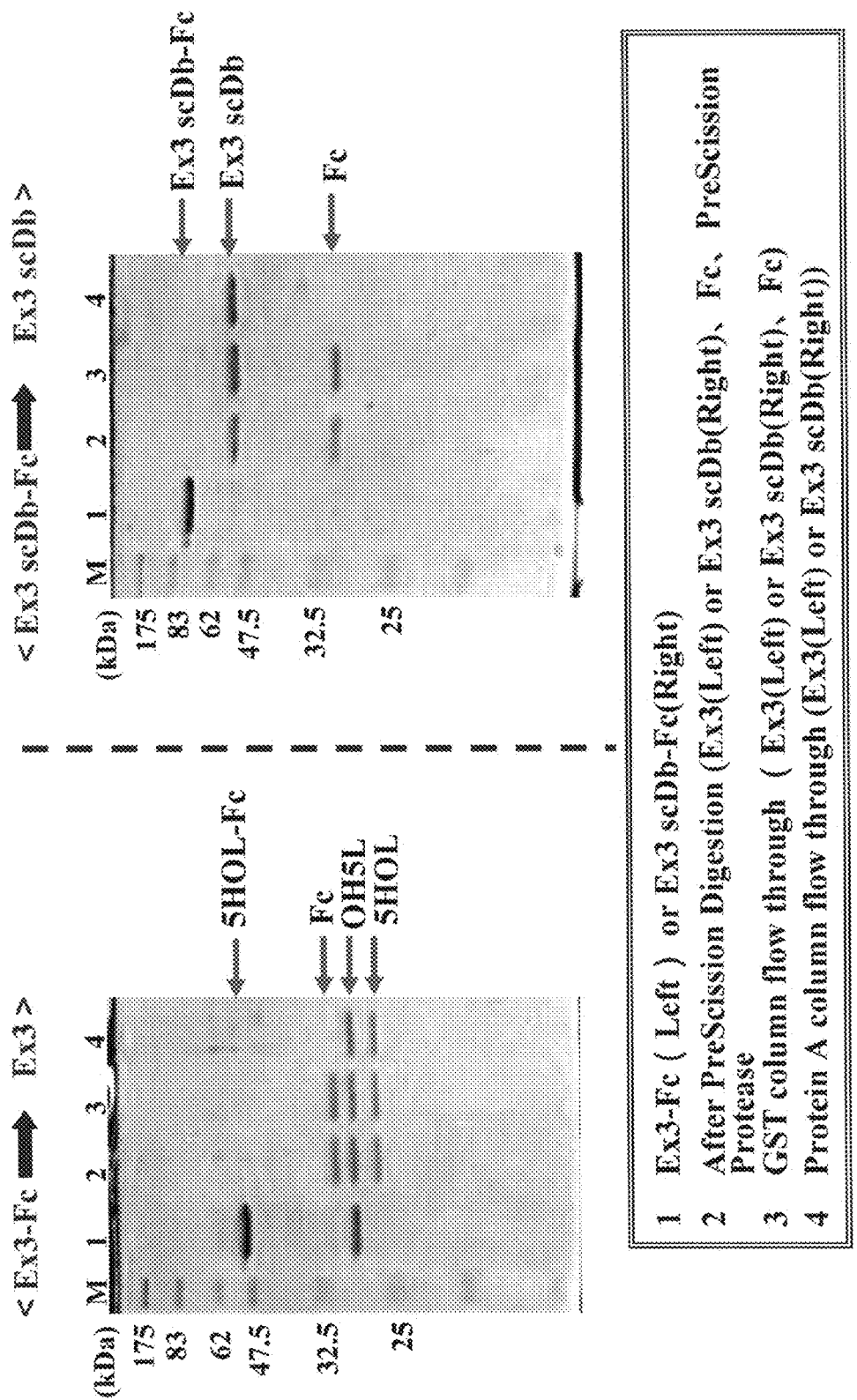
FIG. 12 are photos of SDS-PAGE showing the results of purification of Ex3 and Ex3 scD after the protease-digestion of Ex3-Fc and Ex3 scDb-Fc.

After Ex3-Fc and Ex3 scDb-Fc were digested at the PreSission added with GST-tag with the protease, the PreSission was removed with a column chromatography filled with Glutathione-fixed resin. The digested Fc region and undigested Ex3-Fc and Ex3 scDb-Fc were then removed with Protein A column chromatography to give Ex3 and Ex3 scDb. Molecules in each operation steps were checked with SDS-PAGE. The yield of Ex3 and Ex3 scDb was as high as 49% and 68%, respectively, demonstrating the advantages of the above new method for the preparation of Ex3 and Ex3 scDb with PreSission protease (FIG. 12).

EXAMPLE 8

Figure 13:
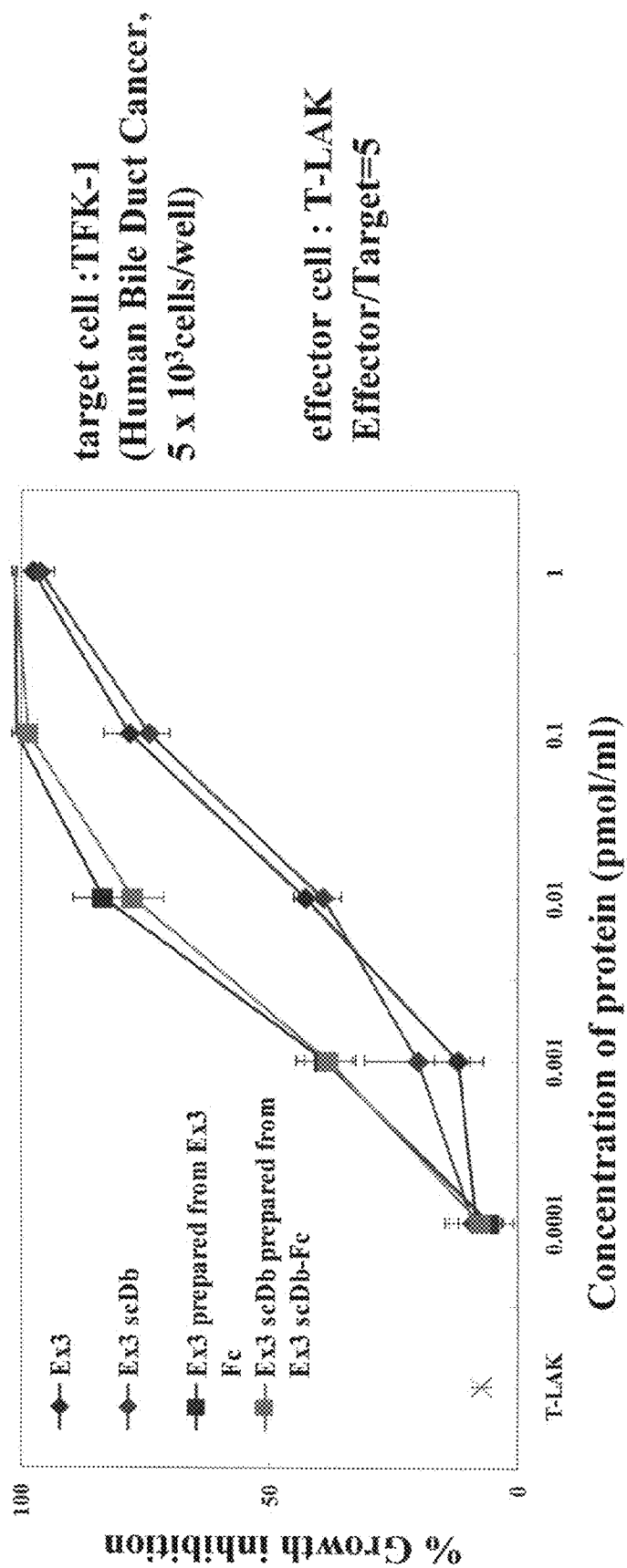
FIG. 13 shows the results of Cytotoxicity Test with use of Ex3 and Ex3 scDb prepared from Ex3-Fc and Ex3 scDb-Fe.

Evaluation of the Function of the Ex3 and Ex3 scDb Prepared from Ex3-Fc and Ex3 scDb-Fc Cytotoxicity test was done in order to compare the Ex3 and Ex3 scDb prepared from Ex3-Fc and Ex3 scDb-Fc by the protease-digestion, and Ex3 and Ex3 scDb prepared directly and purified with IMAC. As a result, it was observed that the two kinds of molecules prepared by the protease digestion have a similar cytotoxicity, which was higher than that of the Ex3 and Ex3 scDb prepared by the conventional method (FIG. 13).

Figure 14:
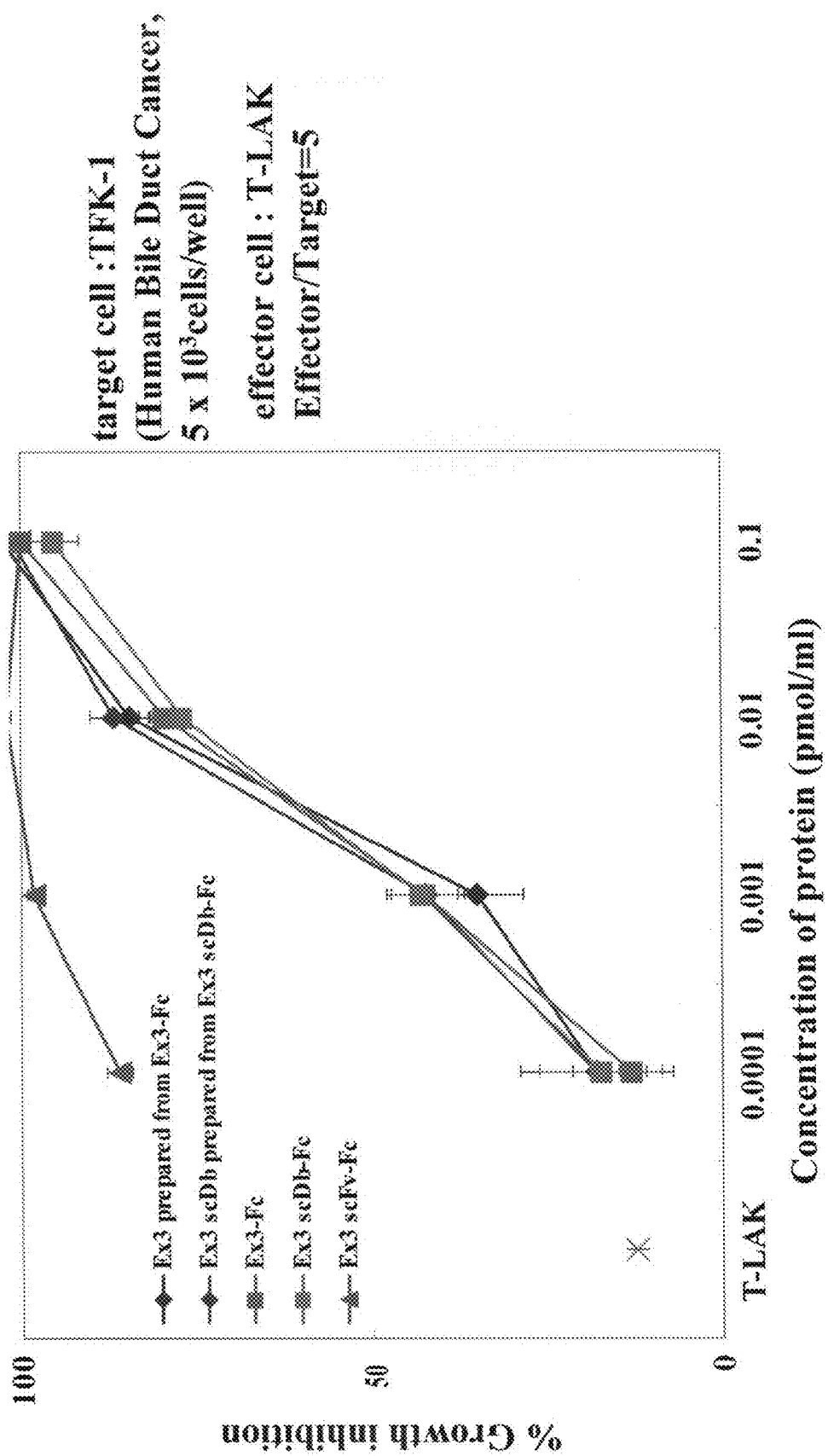
FIG. 14 shows the results of comparison between Ex3 and Ex3 scDb prepared from Ex3-Fc and Ex3 scDb-Fc.

Furthermore, it was shown that the Ex3 and Ex3 scDb prepared from Ex3-Fc and Ex3 scDb-Fc had substantially the same cytotoxicity as that of Fc-fused BsAb, Ex3-Fc and Ex3 scDb-Fc (FIG. 14). It was considered that these results were obtained because the addition of a peptide such as the tag, which had been necessary in the conventional IMAC purification, could be minimized and the extent of purification was high in this new method, demonstrating the advantages of this new production method.

EXAMPLE 9

Evaluation of the Function of Ex3 scFv-FC—In Vivo Treatment Test

TFK-1 cells of $5 \times 10^6$ were subcutaneously injected into SCID mouse ten days after their purchase. After ten days of the transplantation of TFK-1 cells (the diameter of the tumor had become 4-6 mm), the combination of T-LAK cells of $2 \times 10^6$, IL-20 (500 IU) and Ex3, or Ex3scFv-Fc alone was injected through the vein at a tail for successive four days. In every one week, the diameter of tumor was determined so that a volume of the tumor was roughly calculated from its major and minor axes.

Figure 15:
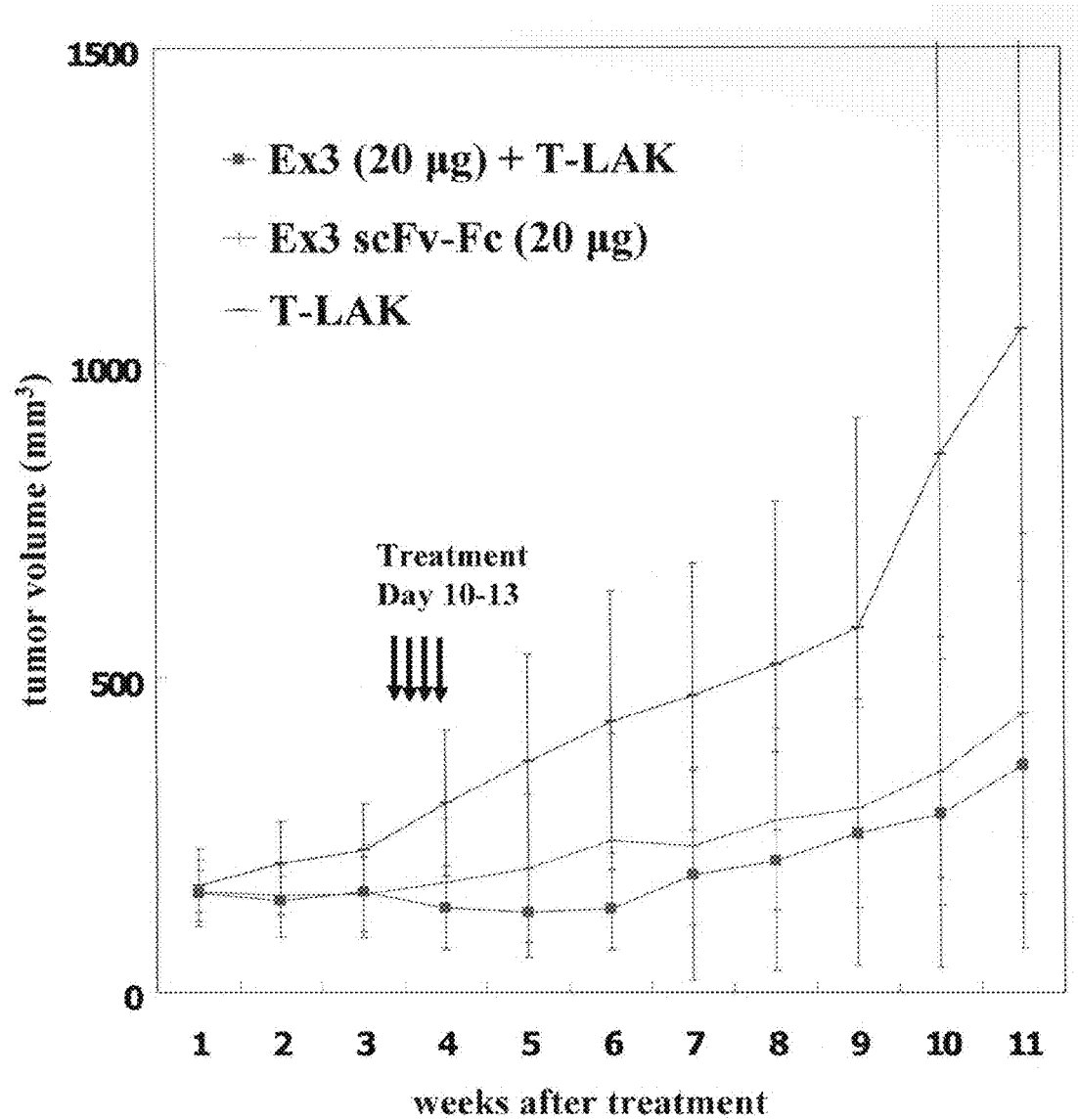
FIG. 15 shows the results of evaluation of the functions of Ex3 scFv-Fc in a treatment test in vivo.

As a result, while the tumor kept on growing in a group of a single administration of T-LAK cells, the previously observed degeneracy effect was reproduced in a group of a single administration of Ex3 at a rate of 20 µg/mouse/day (FIG. 15). On the other hand, Ex3 scFv-Fc could show a sufficient degeneracy effect without co-administration of T-LAK cells. It is considered that these effects were attributed to the increase in valence or the induction of ADCC by the Fc region, which gave us a lot of expectation of its single use for the clinical application.

EXAMPLE 10

Figure 8:
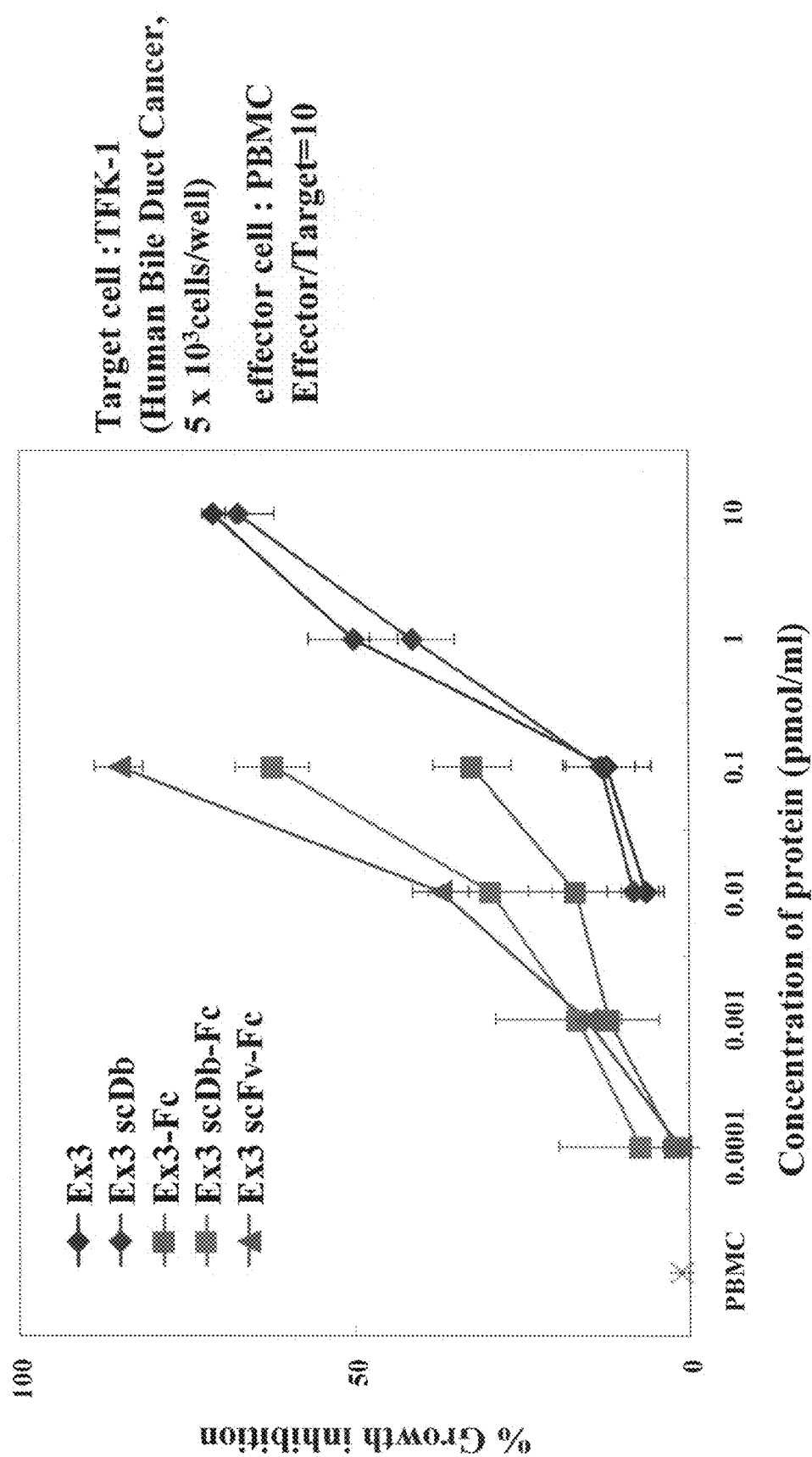
FIG. 8 shows the results of Cytotoxicity Test with use of PBMC.
Figure 16:
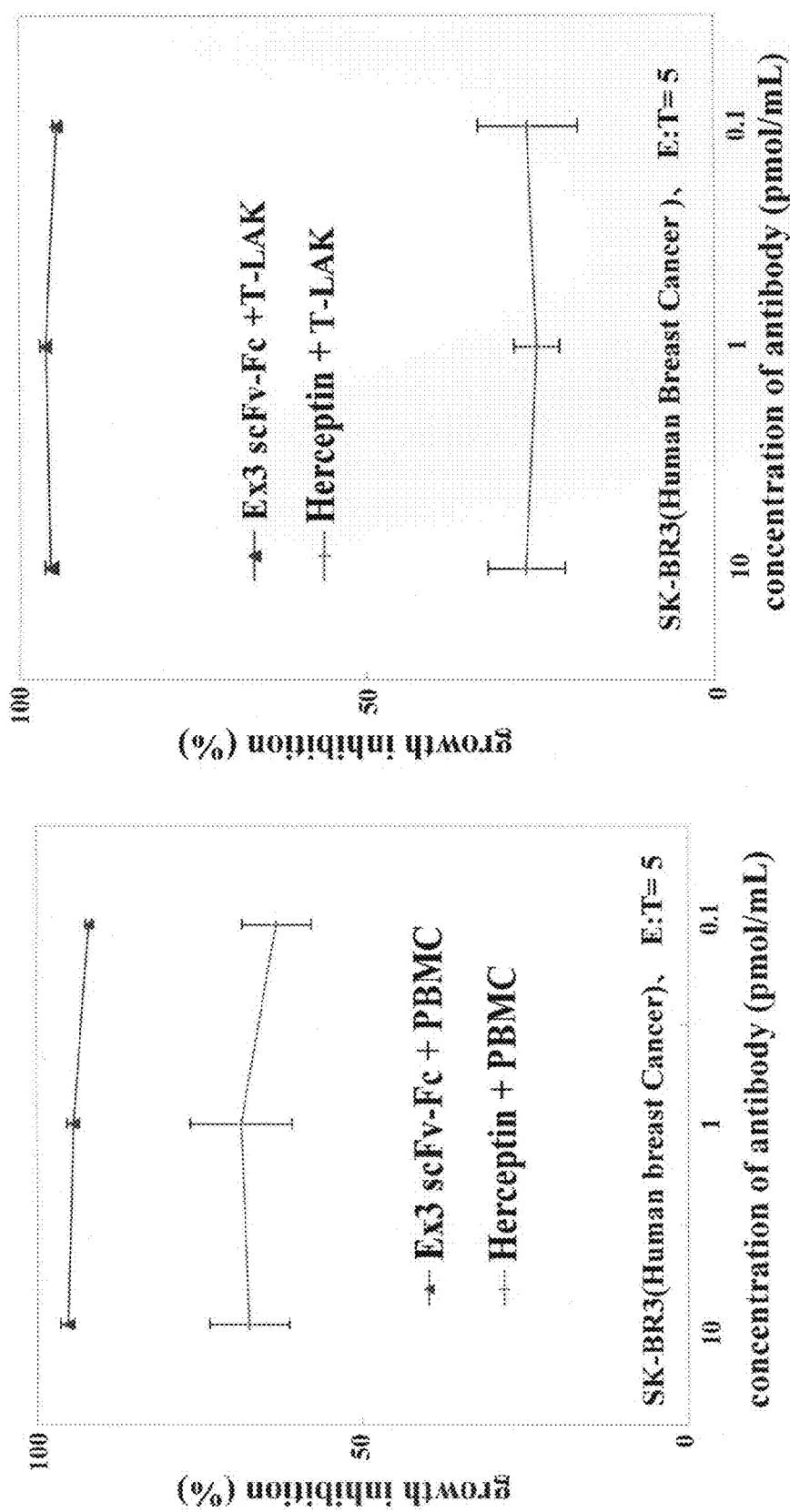
FIG. 16 shows the results of evaluation of the functions of Ex3 scFv-Fc in comparison with a commercially available antibody agent.

Evaluation of the Function of Ex3 scFv-Fc—Comparison with Commercially Available Antibody Agent Comparison test was carried out using a human breast cancer cell line SK-BR3 that was positive for both HER2 recognized by HERCEPTIN • and EGFR recognized by Ex3 scFv-FC. The bispecific antibodies that would induce cytotoxicity through a cross-linking between the lymphocyte and cancer cells showed stronger effects with the use of T-LAK cell as an effector cell than with the use of PBMC (FIG. 7 and FIG. 8). As one of the main function or mechanism of HERCEPTIN • was considered to be ADCC via the Fc region, stronger effects were observed with the use of PBMC comprising a lot of Fc receptors as the effecter cell (FIG. 16). Anyway, Ex3 scFv-FC showed more advantageous effects than HERCEPTIN • with the use of either cell as the effector cell.

EXAMPLE 11

Construction and Evaluation of New Bispecific Antibodies Based on Ex3

Figure 17:
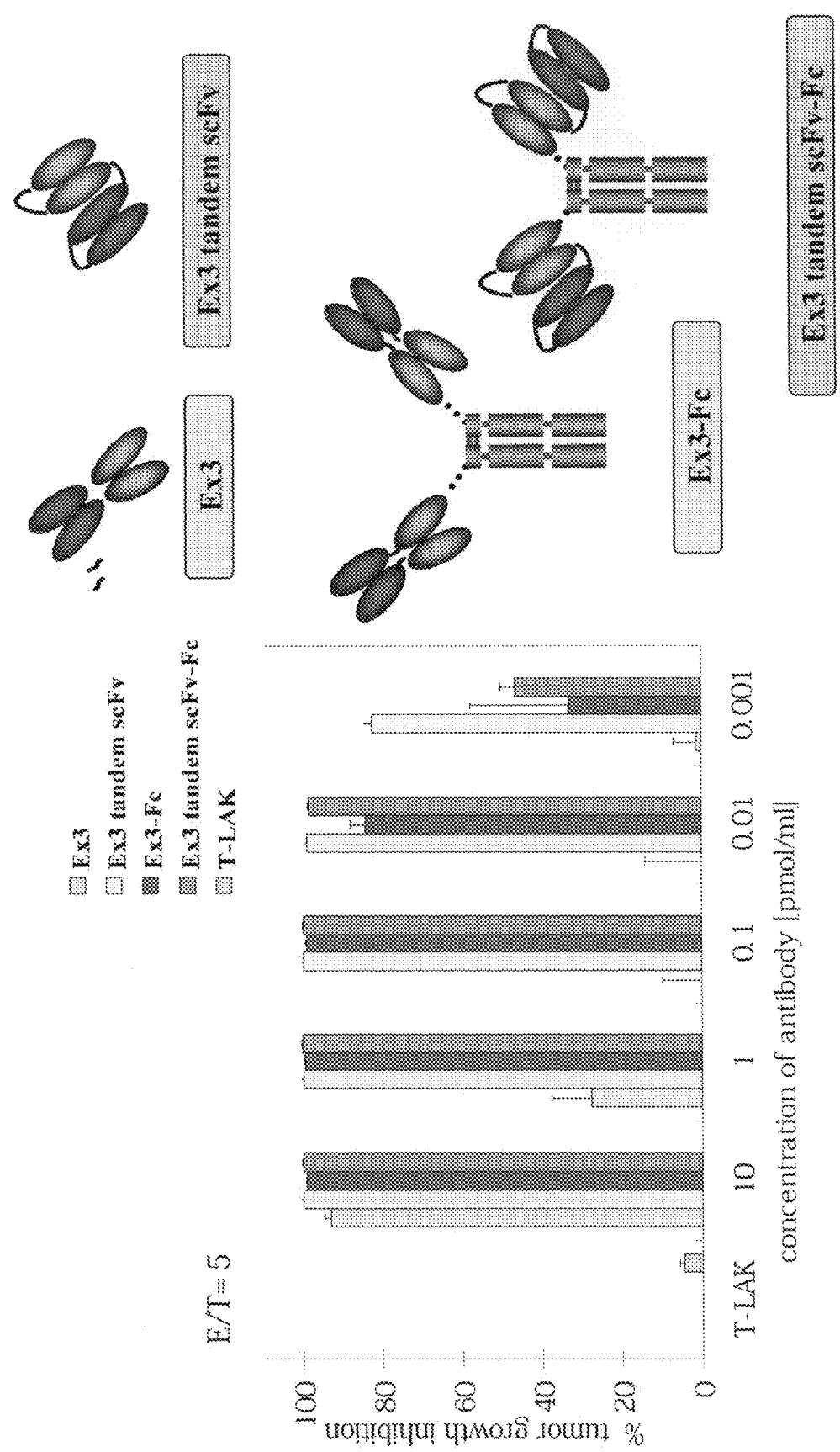
FIG. 17 shows the structures of Ex3 tandem scFv and Ex3 tandem scFv-Fc of the humanized highly functional bispecific antibody according to the present invention, and the results of in vitro Cytotoxicity Test in MTS assay with use of them. Bars for each antibody concentration mean Ex3, Ex3 tandem scFv, Ex3-Fc and Ex3 tandem scFv-Fc in the order of from the left to the right.

Two kinds of molecules were designed in order to construct a more highly functional bispecific antibody as shown in FIG. 17. Thus, Ex3 tandem scFv wherein 528 scFv and OKT3 scFv were linked tandem together via the peptide linker (the sixth type of the present BsAb), and Ex3 tandem scFv-Fc wherein the Fc region was further added to Ex3 tandem scFv (the third type of the present BsAb) were constructed and evaluated.

Each expression vector was prepared on the basis of the expression vectors for 5HL (528 scFv), OHL (OKT3 scFv), and OH-Fc (the H chain of OKT3), in which all of the variable regions was humanized. 5HL and OHL were amplified by PCR using m-n primers and o-b primers, respectively. The PCR products were then mixed, and amplified by PCR using e-b primers, digested with NheI and XhoI, and inserted into pKHI-Neo to give pKHI-Ex3 tandem scFv. The resulting pKHI-Ex3 tandem scFv and OH-Fc were amplified by PCR using e-h primers and i-j primers, respectively. The PCR products were mixed, amplified by PCR using e-j primers, digested with NheI and XhoI, inserted into pKHI-Neo to give pKHI-Ex3 tandem scFv-Fc.

Each expression vector was introduced into CHO cells, screened in the antibiotic-selection medium comprising G418, and purified with Protein A affinity column chromatography (FIG. 4-1).

The cytotoxicity test with MTS Assay in vitro revealed that both Ex3 tandem scFv and Ex3 tandem scFv-Fc showed the effect comparable to or more than that of Ex3-Fc, which were much more advantageous than that of Ex3. It was therefore demonstrated that these bispecific antibodies constructed based on Ex3 have a high utility value.

```
m signal H-5L back primer:
                                    [SEQ ID No.39]
5'-gtaactgcaggtgtccactccgatatcgtgatgacccagagccc-3' n 5H-G1-OH forward primer:
                                    [SEQ ID No.40]
5'-ctgcgaaccgccccgccggccgagctcacggtaacca-3' o 5H-G1-OH back primer:
                                    [SEQ ID No.41]
5'-ccggcggggcggttcgcaggtgcaactggtgcagagc-3'
```

INDUSTRIAL APPLICABILITY

This invention has made it possible to develop an antibody drug (agent) that can show alone a sufficient effect without the co-administration of activated lymphocyte (T-LAK).

What is claimed:

1. A humanized highly functional bispecific antibody comprising humanized variable regions of the heavy chain (5H) and the light chain (5L) of an anti-human EGF receptor 1 antibody 528, and humanized variable regions of the heavy chain (OH) and the light chain (OL) of an anti-CD3 antibody OKT3; comprising one of the following structures:
   (i) a tetravalent antibody comprising two single-chain polypeptides of (5L5H)-(a peptide linker)-(OHOL), and wherein the single-chain polypeptides are bonded to two Fc regions of a human antibody via each hinge region;
   (ii) a tetravalent antibody comprising four single-chain polypeptides, each comprising a VH and a VL region, wherein both of the two VH and two VL regions are replaced by:
      a single-chain Fv (5HL) polypeptide, which comprises humanized variable regions of the heavy chain (5H) and the light chain (5L) of an anti-human EGF receptor 1 antibody 528, and
      a single-chain Fv (OHL) polypeptide, which comprises humanized variable regions of the heavy chain (OH) and the light chain (OL) of an anti-CD3 antibody OKT3,
   respectively, or vice versa;
   or
   (iii) (5L5H)-(a peptide linker)-(OHOL),
   wherein the 5H, 5L, OH and OL have the amino acid sequence of SEQ ID NO: 25, 26, 27 and 28, respectively.

2. The humanized highly functional bispecific antibody of claim 1 comprising the structure (i), wherein the single-chain polypeptide is bonded to the hinge regions via a protease cleavage site.

3. A polypeptide constituting the humanized highly functional bispecific antibody of claim 1 comprising the structure (i).

4. A polypeptide constituting the humanized highly functional bispecific antibody of claim 1 comprising the structure (ii).

5. A composition comprising:
   the humanized highly functional bispecific antibody of any one of claims 1 or 2 as an active ingredient; and
   a pharmaceutical excipient.

6. The humanized functional antibody according to claim 1, wherein 5H consists of SEQ ID NO: 25, 5L consists of SEQ ID NO: 26, OH consists of SEQ ID NO: 27, and OL consists of SEQ ID NO: 28.

* * * * *

SEQUENCE LISTING

<160> NUMBER OF SEQ ID NOS: 41

<210> SEQ ID NO 1
<211> LENGTH: 33
<212> TYPE: DNA
<213> ORGANISM: Artificial Sequence
<220> FEATURE:
<223> OTHER INFORMATION: NcoI-5H back synthetic primer
<220> FEATURE:
<221> NAME/KEY: misc_feature
<222> LOCATION: (1)..(3)
<223> OTHER INFORMATION: n is a, c, g, or t

<400> SEQUENCE: 1
nnnccatggc ccaggtccag ctgcagcagt ctg                33

<210> SEQ ID NO 2
<211> LENGTH: 28
<212> TYPE: DNA
<213> ORGANISM: Artificial Sequence
<220> FEATURE:
<223> OTHER INFORMATION: 5H-EagI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 2
nnncggccga ggagactgtg agagtggt                28

<210> SEQ ID NO 3
<211> LENGTH: 26
<212> TYPE: DNA
<213> ORGANISM: Artificial Sequence
<220> FEATURE:
<223> OTHER INFORMATION: EcoRV-5L back synthetic primer
<220> FEATURE:
<221> NAME/KEY: misc_feature
<222> LOCATION: (1)..(3)
<223> OTHER INFORMATION: n is a, c, g, or t

<400> SEQUENCE: 3
nnngatatcc taatgaccca atctcc                26

<210> SEQ ID NO 4
<211> LENGTH: 29
<212> TYPE: DNA
<213> ORGANISM: Artificial Sequence
<220> FEATURE:
<223> OTHER INFORMATION: 5L-SacII forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 4
nnnccgcggc acgtttgatt tccagcttg                29

<210> SEQ ID NO 5
<211> LENGTH: 32
<212> TYPE: DNA
<213> ORGANISM: Artificial Sequence
<220> FEATURE:
<223> OTHER INFORMATION: NcoI-5H back synthetic primer
<220> FEATURE:
<221> NAME/KEY: misc_feature
<222> LOCATION: (1)..(3)
<223> OTHER INFORMATION: n is a, c, g, or t

<400> SEQUENCE: 5
nnnccatggc ccaggtgcaa ctggttcaga gc                32

```
<210> SEQ ID NO 6
<211> LENGTH: 29
<212> TYPE: DNA
<213> ORGANISM: Artificial Sequence
<220> FEATURE:
<223> OTHER INFORMATION: 5H-EagI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 6
nnncggccga gctcacggta accagcgta                                           29

<210> SEQ ID NO 7
<211> LENGTH: 23
<212> TYPE: DNA
<213> ORGANISM: Artificial Sequence
<220> FEATURE:
<223> OTHER INFORMATION: EcoRV-OL back synthetic primer
<220> FEATURE:
<221> NAME/KEY: misc_feature
<222> LOCATION: (1)..(3)
<223> OTHER INFORMATION: n is a, c, g, or t

<400> SEQUENCE: 7
nnngatatcc agatgaccca gag                                                 23

<210> SEQ ID NO 8
<211> LENGTH: 23
<212> TYPE: DNA
<213> ORGANISM: Artificial Sequence
<220> FEATURE:
<223> OTHER INFORMATION: OL-SacII forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 8
nnnccgcggc gcgggtaatc tgc                                                 23

<210> SEQ ID NO 9
<211> LENGTH: 26
<212> TYPE: DNA
<213> ORGANISM: Artificial Sequence
<220> FEATURE:
<223> OTHER INFORMATION: NcoI-OH back synthetic primer
<220> FEATURE:
<221> NAME/KEY: misc_feature
<222> LOCATION: (1)..(3)
<223> OTHER INFORMATION: n is a, c, g, or t

<400> SEQUENCE: 9
nnnccatggc ccaggtgcaa ctggtg                                              26

<210> SEQ ID NO 10
<211> LENGTH: 23
<212> TYPE: DNA
<213> ORGANISM: Artificial Sequence
<220> FEATURE:
<223> OTHER INFORMATION: OH-EagI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 10
```
nnncggccga gctaacggtc acc                                           23

<210> SEQ ID NO 11
<211> LENGTH: 26
<212> TYPE: DNA
<213> ORGANISM: Artificial Sequence
<220> FEATURE:
<223> OTHER INFORMATION: EcoRV-5L back synthetic primer
<220> FEATURE:
<221> NAME/KEY: misc_feature
<222> LOCATION: (1)..(3)
<223> OTHER INFORMATION: n is a, c, g, or t

<400> SEQUENCE: 11
nnngatatcg tgatgaccca gagccc                                        26

<210> SEQ ID NO 12
<211> LENGTH: 36
<212> TYPE: DNA
<213> ORGANISM: Artificial Sequence
<220> FEATURE:
<223> OTHER INFORMATION: 5L-SacII forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 12
nnnccgcggc gcgtttaatt tccactttgg tgccac                             36

<210> SEQ ID NO 13
<211> LENGTH: 51
<212> TYPE: DNA
<213> ORGANISM: Artificial Sequence
<220> FEATURE:
<223> OTHER INFORMATION: G2 linker-528H back synthetic primer

<400> SEQUENCE: 13
ggcggcggcg gctccggtgg tggtggatcc caggtgcaac tggttcagag c            51

<210> SEQ ID NO 14
<211> LENGTH: 28
<212> TYPE: DNA
<213> ORGANISM: Artificial Sequence
<220> FEATURE:
<223> OTHER INFORMATION: c-myc & His-tag-XhoI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 14
nnncggccga ggagactgtg agagtggt                                      28

<210> SEQ ID NO 15
<211> LENGTH: 41
<212> TYPE: DNA
<213> ORGANISM: Artificial Sequence
<220> FEATURE:
<223> OTHER INFORMATION: signal H-OH back synthetic primer

<400> SEQUENCE: 15
gtaactgcag gtgtccactc ccaggtgcaa ctggtgcaga g                       41

<210> SEQ ID NO 16
<211> LENGTH: 78
<212> TYPE: DNA
<213> ORGANISM: Artificial Sequence

```
<220> FEATURE:
<223> OTHER INFORMATION: 5L-G3 linker forward synthetic primer

<400> SEQUENCE: 16
ggagccgccg ccgccagaac caccaccacc agaaccacca ccacctgcag ccgcggcgcg      60
tttaatttcc actttggt                                                   78

<210> SEQ ID NO 17
<211> LENGTH: 70
<212> TYPE: DNA
<213> ORGANISM: Artificial Sequence
<220> FEATURE:
<223> OTHER INFORMATION: NheI-signal H back synthetic primer
<220> FEATURE:
<221> NAME/KEY: misc_feature
<222> LOCATION: (1)..(3)
<223> OTHER INFORMATION: n is a, c, g, or t

<400> SEQUENCE: 17
nnngctagcc accatggatt gggtgtggac cttgctattc ctgttgtcag taactgcagg      60
tgtccactcc                                                            70

<210> SEQ ID NO 18
<211> LENGTH: 39
<212> TYPE: DNA
<213> ORGANISM: Artificial Sequence
<220> FEATURE:
<223> OTHER INFORMATION: G4 linker-BamHI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 18
nnnggatcca ccaccaccgg agccgccgcc gccagaacc                             39

<210> SEQ ID NO 19
<211> LENGTH: 41
<212> TYPE: DNA
<213> ORGANISM: Artificial Sequence
<220> FEATURE:
<223> OTHER INFORMATION: signal H-5H back synthetic primer

<400> SEQUENCE: 19
gtaactgcag gtgtccactc ccaggtgcaa ctggttcaga g                          41

<210> SEQ ID NO 20
<211> LENGTH: 42
<212> TYPE: DNA
<213> ORGANISM: Artificial Sequence
<220> FEATURE:
<223> OTHER INFORMATION: OL-precission forward synthetic primer

<400> SEQUENCE: 20
cccctggaac agaacttcca gggcgcgggt aatctgcagt tt                         42

<210> SEQ ID NO 21
<211> LENGTH: 42
<212> TYPE: DNA
<213> ORGANISM: Artificial Sequence
<220> FEATURE:
<223> OTHER INFORMATION: precission-hinge back synthetic primer

<400> SEQUENCE: 21
ctggaagttc tgttccaggg gcccgacaaa actcacacat gc                         42
```

<210> SEQ ID NO 22
<211> LENGTH: 33
<212> TYPE: DNA
<213> ORGANISM: Artificial Sequence
<220> FEATURE:
<223> OTHER INFORMATION: CH3-XhoI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 22
nnnctcgagt catttacccg agacaggga gag                33

<210> SEQ ID NO 23
<211> LENGTH: 30
<212> TYPE: DNA
<213> ORGANISM: Artificial Sequence
<220> FEATURE:
<223> OTHER INFORMATION: hOL-XhoI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 23
nnnctcgagc gggtaatctg cagtttggta                30

<210> SEQ ID NO 24
<211> LENGTH: 41
<212> TYPE: DNA
<213> ORGANISM: Artificial Sequence
<220> FEATURE:
<223> OTHER INFORMATION: h528L-NarI forward synthetic primer
<220> FEATURE:
<221> NAME/KEY: misc_feature
<222> LOCATION: (1)..(3)
<223> OTHER INFORMATION: n is a, c, g, or t

<400> SEQUENCE: 24
nnnggcgccg ccacagtgcg tttaatttcc actttggtgc c                41

<210> SEQ ID NO 25
<211> LENGTH: 354
<212> TYPE: DNA
<213> ORGANISM: Artificial Sequence
<220> FEATURE:
<223> OTHER INFORMATION: Synthetic chimeric Sequence (h5H)
<220> FEATURE:
<221> NAME/KEY: CDS
<222> LOCATION: (1)..(354)

<400> SEQUENCE: 25

```
cag gtg caa ctg gtt cag agc ggc gcg gaa gtg aaa aag ccg ggc gcg      48
Gln Val Gln Leu Val Gln Ser Gly Ala Glu Val Lys Lys Pro Gly Ala
1               5                   10                  15 tcg gtt aaa gtg agc tgc aaa gcc tca ggc tat acc ttt acg agc tac      96
Ser Val Lys Val Ser Cys Lys Ala Ser Gly Tyr Thr Phe Thr Ser Tyr
            20                  25                  30 tgg atg cat tgg gtg cgc cag gcc ccg ggt cag ggc ctg gaa tgg atg     144
Trp Met His Trp Val Arg Gln Ala Pro Gly Gln Gly Leu Glu Trp Met
        35                  40                  45 ggt aac att tat ccg ggc agc ggt ggc acc aac tat gcg gaa aaa ttt     192
Gly Asn Ile Tyr Pro Gly Ser Gly Gly Thr Asn Tyr Ala Glu Lys Phe
    50                  55                  60 aag aac cgc gtg acc atg acg cgt gat acc agc att tcg acg gcc tat     240
Lys Asn Arg Val Thr Met Thr Arg Asp Thr Ser Ile Ser Thr Ala Tyr
```

```
atg gaa ctg agc cgc ctg cgt agc gat gac acc gcc gtg tat tac tgc      288
Met Glu Leu Ser Arg Leu Arg Ser Asp Asp Thr Ala Val Tyr Tyr Cys
                85                  90                  95 gcg cgc agt ggc ggt ccg tat ttt ttc gat tac tgg ggc cag ggt acg      336
Ala Arg Ser Gly Gly Pro Tyr Phe Phe Asp Tyr Trp Gly Gln Gly Thr
            100                 105                 110 ctg gtt acc gtg agc tcg                                              354
Leu Val Thr Val Ser Ser
        115

<210> SEQ ID NO 26
<211> LENGTH: 339
<212> TYPE: DNA
<213> ORGANISM: Artificial Sequence
<220> FEATURE:
<223> OTHER INFORMATION: Synthetic chimeric Sequence (h5L)
<220> FEATURE:
<221> NAME/KEY: CDS
<222> LOCATION: (1)..(339)

<400> SEQUENCE: 26 gat att gtg atg acc cag agc ccg ctg agc ctg ccg gtg acc cca ggc       48
Asp Ile Val Met Thr Gln Ser Pro Leu Ser Leu Pro Val Thr Pro Gly
1               5                   10                  15 gaa ccg gcg tcg att agc tgc cgc agc tcg cag aac atc gtg cat aat       96
Glu Pro Ala Ser Ile Ser Cys Arg Ser Ser Gln Asn Ile Val His Asn
            20                  25                  30 aac ggc att acc tat ctg gaa tgg tat ctg cag aaa ccg ggc caa agc      144
Asn Gly Ile Thr Tyr Leu Glu Trp Tyr Leu Gln Lys Pro Gly Gln Ser
        35                  40                  45 ccg cag ctg tta att tat aaa gtg agc gat cgc ttt agc ggc gtg ccg      192
Pro Gln Leu Leu Ile Tyr Lys Val Ser Asp Arg Phe Ser Gly Val Pro
    50                  55                  60 gat cgc ttt tcg ggc agc ggt agt ggc acc gat ttt acg ctg aaa att      240
Asp Arg Phe Ser Gly Ser Gly Ser Gly Thr Asp Phe Thr Leu Lys Ile
65                  70                  75                  80 agc cgc gtg gaa gcg gag gat gtt ggc gtg tat tac tgc ttt cag ggc      288
Ser Arg Val Glu Ala Glu Asp Val Gly Val Tyr Tyr Cys Phe Gln Gly
                85                  90                  95 agc cat atc ccg cca acc ttt ggc caa ggc acc aaa gtg gaa att aaa      336
Ser His Ile Pro Pro Thr Phe Gly Gln Gly Thr Lys Val Glu Ile Lys
            100                 105                 110 cgc                                                                  339
Arg

<210> SEQ ID NO 27
<211> LENGTH: 357
<212> TYPE: DNA
<213> ORGANISM: Artificial Sequence
<220> FEATURE:
<223> OTHER INFORMATION: Synthetic chimeric Sequence (hOH)
<220> FEATURE:
<221> NAME/KEY: CDS
<222> LOCATION: (1)..(357)

<400> SEQUENCE: 27 cag gtg caa ctg gtg cag agc ggc ggt ggc gtt gtg cag ccg ggc cgc       48
Gln Val Gln Leu Val Gln Ser Gly Gly Gly Val Val Gln Pro Gly Arg
1               5                   10                  15 agc ctg cgc ctg tct tgc aaa gcg agc ggc tat acc ttt acg cgc tat       96
Ser Leu Arg Leu Ser Cys Lys Ala Ser Gly Tyr Thr Phe Thr Arg Tyr
            20                  25                  30
```

| | | |
|---|---|---|
| acc atg cat tgg gtg cgc cag gcg ccg ggc aaa ggt ctg gaa tgg att<br>Thr Met His Trp Val Arg Gln Ala Pro Gly Lys Gly Leu Glu Trp Ile<br>35 40 45 | | 144 |
| ggc tat att aac ccg tct cgc ggc tat acc aac tat aat cag aaa gtg<br>Gly Tyr Ile Asn Pro Ser Arg Gly Tyr Thr Asn Tyr Asn Gln Lys Val<br>50 55 60 | | 192 |
| aaa gat cgc ttt acc att agc cgc gat aac tct aaa aac acc gcg ttt<br>Lys Asp Arg Phe Thr Ile Ser Arg Asp Asn Ser Lys Asn Thr Ala Phe<br>65 70 75 80 | | 240 |
| ctg cag atg gat agc ctg cgc ccg gaa gat acc ggt gtg tat ttt tgc<br>Leu Gln Met Asp Ser Leu Arg Pro Glu Asp Thr Gly Val Tyr Phe Cys<br>85 90 95 | | 288 |
| gcg cgc tac tat gat gac cat tat agc ctg gat tat tgg ggc cag ggc<br>Ala Arg Tyr Tyr Asp Asp His Tyr Ser Leu Asp Tyr Trp Gly Gln Gly<br>100 105 110 | | 336 |
| acc ccg gtg acc gtt agc tcg<br>Thr Pro Val Thr Val Ser Ser<br>115 | | 357 |

<210> SEQ ID NO 28
<211> LENGTH: 321
<212> TYPE: DNA
<213> ORGANISM: Artificial Sequence
<220> FEATURE:
<223> OTHER INFORMATION: Synthetic Chimeric Sequence (hOL)
<220> FEATURE:
<221> NAME/KEY: CDS
<222> LOCATION: (1)..(321)

<400> SEQUENCE: 28

| | | |
|---|---|---|
| gat atc cag atg acc cag agc ccg agc tct ctg agc gcg agc gtg ggc<br>Asp Ile Gln Met Thr Gln Ser Pro Ser Ser Leu Ser Ala Ser Val Gly<br>1 5 10 15 | | 48 |
| gat cgc gtg acc att acg tgc agc gcg tct agc tct gtg agc tat atg<br>Asp Arg Val Thr Ile Thr Cys Ser Ala Ser Ser Ser Val Ser Tyr Met<br>20 25 30 | | 96 |
| aac tgg tac cag caa acc cca ggc aaa gcg ccg aaa cgc tgg att tat<br>Asn Trp Tyr Gln Gln Thr Pro Gly Lys Ala Pro Lys Arg Trp Ile Tyr<br>35 40 45 | | 144 |
| gat acc agc aaa ctg gcg agc ggc gtg ccg agc cgc ttt agc ggc tct<br>Asp Thr Ser Lys Leu Ala Ser Gly Val Pro Ser Arg Phe Ser Gly Ser<br>50 55 60 | | 192 |
| ggt agc ggc acc gat tat acg ttt acc att agc tct ctg cag ccg gaa<br>Gly Ser Gly Thr Asp Tyr Thr Phe Thr Ile Ser Ser Leu Gln Pro Glu<br>65 70 75 80 | | 240 |
| gat att gcg acc tat tac tgc cag caa tgg agc tct aac ccg ttt acc<br>Asp Ile Ala Thr Tyr Tyr Cys Gln Gln Trp Ser Ser Asn Pro Phe Thr<br>85 90 95 | | 288 |
| ttt ggc cag ggt acc aaa ctg cag att acc cgc<br>Phe Gly Gln Gly Thr Lys Leu Gln Ile Thr Arg<br>100 105 | | 321 |

<210> SEQ ID NO 29
<211> LENGTH: 315
<212> TYPE: DNA
<213> ORGANISM: Homo sapiens
<220> FEATURE:
<221> NAME/KEY: misc_feature
<223> OTHER INFORMATION: CH1
<220> FEATURE:
<221> NAME/KEY: CDS
<222> LOCATION: (1)..(315)

<400> SEQUENCE: 29

```
tcg agt gcc tcc acc aag ggc cca tcg gtc ttc ccc ctg gca ccc tcc      48
Ser Ser Ala Ser Thr Lys Gly Pro Ser Val Phe Pro Leu Ala Pro Ser
1               5                   10                  15 tcc aag agc acc tct ggg ggc aca gcg gcc ctg ggc tgc ctg gtc aag      96
Ser Lys Ser Thr Ser Gly Gly Thr Ala Ala Leu Gly Cys Leu Val Lys
            20                  25                  30 gac tac ttc ccc gaa ccg gtg acg gtg tcg tgg aac tca ggc gcc ctg     144
Asp Tyr Phe Pro Glu Pro Val Thr Val Ser Trp Asn Ser Gly Ala Leu
        35                  40                  45 acc agc ggc gtg cac acc ttc ccg gct gtc cta cag tcc tca gga ctc     192
Thr Ser Gly Val His Thr Phe Pro Ala Val Leu Gln Ser Ser Gly Leu
    50                  55                  60 tac tcc ctc agc agc gtg gtg acc gtg ccc tcc agc agc ttg ggc acc     240
Tyr Ser Leu Ser Ser Val Val Thr Val Pro Ser Ser Ser Leu Gly Thr
65                  70                  75                  80 cag acc tac atc tgc aac gtg aat cac aag ccc agc aac acc aag gtg     288
Gln Thr Tyr Ile Cys Asn Val Asn His Lys Pro Ser Asn Thr Lys Val
                85                  90                  95 gac aag aaa gtt gag ccc aaa tct tgt                                 315
Asp Lys Lys Val Glu Pro Lys Ser Cys
            100                 105

<210> SEQ ID NO 30
<211> LENGTH: 651
<212> TYPE: DNA
<213> ORGANISM: Homo sapiens
<220> FEATURE:
<221> NAME/KEY: misc_feature
<223> OTHER INFORMATION: CH2 & CH3
<220> FEATURE:
<221> NAME/KEY: CDS
<222> LOCATION: (1)..(651)

<400> SEQUENCE: 30 gca cct gaa ctc ctg ggg gga ccg tca gtc ttc ctc ttc ccc cca aaa      48
Ala Pro Glu Leu Leu Gly Gly Pro Ser Val Phe Leu Phe Pro Pro Lys
1               5                   10                  15 ccc aag gac acc ctc atg atc tcc cgg acc cct gag gtc aca tgc gtg      96
Pro Lys Asp Thr Leu Met Ile Ser Arg Thr Pro Glu Val Thr Cys Val
            20                  25                  30 gtg gtg gac gtg agc cac gaa gac cct gag gtc aag ttc aac tgg tac     144
Val Val Asp Val Ser His Glu Asp Pro Glu Val Lys Phe Asn Trp Tyr
        35                  40                  45 gtg gac ggc gtg gag gtg cat aat gcc aag aca aag ccg cgg gag gag     192
Val Asp Gly Val Glu Val His Asn Ala Lys Thr Lys Pro Arg Glu Glu
    50                  55                  60 cag tac aac agc acg tac cgt gtg gtc agc gtc ctc acc gtc ctg cac     240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa     288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa ggg cag     336
Ala Leu Pro Ala Pro Ile Glu Lys Thr Ile Ser Lys Ala Lys Gly Gln
            100                 105                 110 ccc cga gaa cca cag gtg tac acc ctg ccc cca tcc cgg gat gag ctg     384
Pro Arg Glu Pro Gln Val Tyr Thr Leu Pro Pro Ser Arg Asp Glu Leu
        115                 120                 125 acc aag aac cag gtc agc ctg acc tgc ctg gtc aaa ggc ttc tat ccc     432
Thr Lys Asn Gln Val Ser Leu Thr Cys Leu Val Lys Gly Phe Tyr Pro
    130                 135                 140
```

```
agc gac atc gcc gtg gag tgg gag agc aat ggg cag ccg gag aac aac      480
Ser Asp Ile Ala Val Glu Trp Glu Ser Asn Gly Gln Pro Glu Asn Asn
145                 150                 155                 160 tac aag acc acg cct ccc gtg ctg gac tcc gac ggc tcc ttc ttc ctc      528
Tyr Lys Thr Thr Pro Pro Val Leu Asp Ser Asp Gly Ser Phe Phe Leu
                165                 170                 175 tac agc aag ctc acc gtg gac aag agc agg tgg cag cag ggg aac gtc      576
Tyr Ser Lys Leu Thr Val Asp Lys Ser Arg Trp Gln Gln Gly Asn Val
            180                 185                 190 ttc tca tgc tcc gtg atg cat gag gct ctg cac aac cac tac acg cag      624
Phe Ser Cys Ser Val Met His Glu Ala Leu His Asn His Tyr Thr Gln
        195                 200                 205 aag agc ctc tcc ctg tct ccg ggt aaa                                   651
Lys Ser Leu Ser Leu Ser Pro Gly Lys
    210                 215

<210> SEQ ID NO 31
<211> LENGTH: 24
<212> TYPE: DNA
<213> ORGANISM: Homo sapiens
<220> FEATURE:
<221> NAME/KEY: misc_feature
<223> OTHER INFORMATION: Presission Recognition Site
<220> FEATURE:
<221> NAME/KEY: CDS
<222> LOCATION: (1)..(24)

<400> SEQUENCE: 31 ctg gaa gtt ctg ttc cag ggg ccc                                       24
Leu Glu Val Leu Phe Gln Gly Pro
1               5

<210> SEQ ID NO 32
<211> LENGTH: 30
<212> TYPE: DNA
<213> ORGANISM: Homo sapiens
<220> FEATURE:
<221> NAME/KEY: misc_feature
<223> OTHER INFORMATION: Hinge
<220> FEATURE:
<221> NAME/KEY: CDS
<222> LOCATION: (1)..(30)

<400> SEQUENCE: 32 gac aaa act cac aca tgc cca ccg tgc cca                               30
Asp Lys Thr His Thr Cys Pro Pro Cys Pro
1               5                   10

<210> SEQ ID NO 33
<211> LENGTH: 318
<212> TYPE: DNA
<213> ORGANISM: Homo sapiens
<220> FEATURE:
<221> NAME/KEY: misc_feature
<223> OTHER INFORMATION: CL
<220> FEATURE:
<221> NAME/KEY: CDS
<222> LOCATION: (1)..(318)

<400> SEQUENCE: 33 act gtg gcg gcg cca tct gtc ttc atc ttc ccg cca tct gat gag cag       48
Thr Val Ala Ala Pro Ser Val Phe Ile Phe Pro Pro Ser Asp Glu Gln
1               5                   10                  15 ttg aaa tct gga act gcc tct gtt gtg tgc ctg ctg aat aac ttc tat       96
Leu Lys Ser Gly Thr Ala Ser Val Val Cys Leu Leu Asn Asn Phe Tyr
            20                  25                  30
```

-continued

| | | |
|---|---|---|
| ccc aga gag gcc aaa gta cag tgg aag gtg gat aac gcc ctc caa tcg<br>Pro Arg Glu Ala Lys Val Gln Trp Lys Val Asp Asn Ala Leu Gln Ser<br>     35                    40                    45 | | 144 |
| ggt aac tcc cag gag agt gtc aca gag cag gac agc aag gac agc acc<br>Gly Asn Ser Gln Glu Ser Val Thr Glu Gln Asp Ser Lys Asp Ser Thr<br>50                      55                    60 | | 192 |
| tac agc ctc agc agc acc ctg acg ctg agc aaa gca gac tac gag aaa<br>Tyr Ser Leu Ser Ser Thr Leu Thr Leu Ser Lys Ala Asp Tyr Glu Lys<br>65                      70                    75                    80 | | 240 |
| cac aaa gtc tac gcc tgc gaa gtc acc cat cag ggc ctg agc tcg ccc<br>His Lys Val Tyr Ala Cys Glu Val Thr His Gln Gly Leu Ser Ser Pro<br>                    85                    90                    95 | | 288 |
| gtc aca aag agc ttc aac agg gga gag tgt<br>Val Thr Lys Ser Phe Asn Arg Gly Glu Cys<br>          100                    105 | | 318 |

<210> SEQ ID NO 34
<211> LENGTH: 18
<212> TYPE: DNA
<213> ORGANISM: Artificial Sequence
<220> FEATURE:
<223> OTHER INFORMATION: Synthetic G1 linker
<220> FEATURE:
<221> NAME/KEY: CDS
<222> LOCATION: (1)..(18)

<400> SEQUENCE: 34

| | |
|---|---|
| gcc ggc ggg ggc ggt tcg<br>Ala Gly Gly Gly Gly Ser<br>1              5 | 18 |

<210> SEQ ID NO 35
<211> LENGTH: 48
<212> TYPE: DNA
<213> ORGANISM: Artificial Sequence
<220> FEATURE:
<223> OTHER INFORMATION: Synthetic G3 linker
<220> FEATURE:
<221> NAME/KEY: CDS
<222> LOCATION: (1)..(48)

<400> SEQUENCE: 35

| | |
|---|---|
| gcc ggc ggg ggc ggt agc ggc ggt ggc ggg tcg ggc ggt ggc gga tcg<br>Ala Gly Gly Gly Gly Ser Gly Gly Gly Gly Ser Gly Gly Gly Gly Ser<br>1              5                    10                    15 | 48 |

<210> SEQ ID NO 36
<211> LENGTH: 72
<212> TYPE: DNA
<213> ORGANISM: Artificial Sequence
<220> FEATURE:
<223> OTHER INFORMATION: Synthetic G4 linker
<220> FEATURE:
<221> NAME/KEY: CDS
<222> LOCATION: (1)..(72)

<400> SEQUENCE: 36

| | |
|---|---|
| gcc gcg gct gca ggt ggt ggt ggt tct ggt ggt ggt ggt tct ggc ggc<br>Ala Ala Ala Ala Gly Gly Gly Gly Ser Gly Gly Gly Gly Ser Gly Gly<br>1              5                    10                    15 | 48 |
| ggc tcc ggt ggt ggt gga tcc<br>Gly Gly Ser Gly Gly Gly Gly Ser<br>          20 | 72 |

<210> SEQ ID NO 37
<211> LENGTH: 57

```
<212> TYPE: DNA
<213> ORGANISM: Artificial Sequence
<220> FEATURE:
<223> OTHER INFORMATION: Synthetic signal peptide
<220> FEATURE:
<221> NAME/KEY: CDS
<222> LOCATION: (1)..(57)

<400> SEQUENCE: 37 atg gat tgg gtg tgg acc ttg cta ttc ctg ttg tca gta act gca ggt    48
Met Asp Trp Val Trp Thr Leu Leu Phe Leu Leu Ser Val Thr Ala Gly
1               5                   10                  15 gtc cac tcc                                                        57
Val His Ser <210> SEQ ID NO 38
<211> LENGTH: 87
<212> TYPE: DNA
<213> ORGANISM: Artificial Sequence
<220> FEATURE:
<223> OTHER INFORMATION: Synthetic c-myc & His tag
<220> FEATURE:
<221> NAME/KEY: CDS
<222> LOCATION: (1)..(87)

<400> SEQUENCE: 38 gcc gcg gct gca gaa caa aaa ctc atc tca gaa gag gat ctg aat cta    48
Ala Ala Ala Ala Glu Gln Lys Leu Ile Ser Glu Glu Asp Leu Asn Leu
1               5                   10                  15 ggg ggt ggc atg cgc ggc tcg cac cat cat cac cac cat                87
Gly Gly Gly Met Arg Gly Ser His His His His His His
                20                  25

<210> SEQ ID NO 39
<211> LENGTH: 44
<212> TYPE: DNA
<213> ORGANISM: Artificial Sequence
<220> FEATURE:
<223> OTHER INFORMATION: signal H-5L back synthetic primer

<400> SEQUENCE: 39
gtaactgcag gtgtccactc cgatatcgtg atgacccaga gccc                   44

<210> SEQ ID NO 40
<211> LENGTH: 38
<212> TYPE: DNA
<213> ORGANISM: Artificial Sequence
<220> FEATURE:
<223> OTHER INFORMATION: 5H-G1-OH forward synthetic primer

<400> SEQUENCE: 40
ctgcgaaccg cccccgccgg ccgagctcac ggtaacca                          38

<210> SEQ ID NO 41
<211> LENGTH: 38
<212> TYPE: DNA
<213> ORGANISM: Artificial Sequence
<220> FEATURE:
<223> OTHER INFORMATION: 5H-G1-OH back synthetic primer

<400> SEQUENCE: 41
ccggcggggg cggttcgcag gtgcaactgg tgcagagc                          38
```